(12) United States Patent
Fulkerson et al.

(10) Patent No.: US 9,220,522 B2
(45) Date of Patent: Dec. 29, 2015

(54) EMBOLUS REMOVAL SYSTEMS WITH BASKETS

(75) Inventors: John Fulkerson, Rancho Santa Margarita, CA (US); David A. Ferrera, Redondo Beach, CA (US)

(73) Assignee: Covidien LP, Mansfield, MA (US)

( * ) Notice: Subject to any disclaimer, the term of this patent is extended or adjusted under 35 U.S.C. 154(b) by 199 days.

(21) Appl. No.: 12/182,370

(22) Filed: Jul. 30, 2008

(65) Prior Publication Data

US 2009/0105722 A1  Apr. 23, 2009

Related U.S. Application Data

(60) Provisional application No. 60/980,736, filed on Oct. 17, 2007, provisional application No. 60/987,384, filed on Nov. 12, 2007, provisional application No. 61/015,154, filed on Dec. 19, 2007, provisional application No. 61/044,392, filed on Apr. 11, 2008, provisional application No. 61/057,613, filed on May 30, 2008.

(51) Int. Cl.
| | |
|---|---|
| *A61B 17/22* | (2006.01) |
| *A61B 17/24* | (2006.01) |
| *A61B 17/221* | (2006.01) |
| *A61F 2/01* | (2006.01) |
| *A61M 25/09* | (2006.01) |

(52) U.S. Cl.
CPC .............. *A61B 17/221* (2013.01); *A61F 2/013* (2013.01); *A61M 25/09* (2013.01); *A61M 25/09025* (2013.01); *A61B 2017/2212* (2013.01); *A61B 2017/22039* (2013.01); *A61B 2017/22094* (2013.01); *A61F 2002/018* (2013.01); *A61F 2230/0006* (2013.01); *A61F 2230/0067* (2013.01)

(58) Field of Classification Search
USPC .................. 606/200, 113, 114, 159, 198, 127
See application file for complete search history.

(56) References Cited

U.S. PATENT DOCUMENTS

| | | | |
|---|---|---|---|
| 2,709,999 | A | 6/1955 | Nagel |
| 3,174,851 | A | 3/1965 | Buehler et al. |
| 3,351,463 | A | 11/1967 | Rozner et al. |
| 3,506,171 | A | 4/1970 | Rupert |
| 3,753,700 | A | 8/1973 | Harrison et al. |
| 4,650,466 | A | 3/1987 | Luther |
| 4,993,481 | A | 2/1991 | Kamimoto et al. |
| 4,998,539 | A | 3/1991 | Delsanti |

(Continued)

FOREIGN PATENT DOCUMENTS

| | | |
|---|---|---|
| EP | 0321912 | 6/1989 |
| EP | 820729 A1 | 1/1998 |

(Continued)

OTHER PUBLICATIONS

T.W. Duerig, D.E. Tolomeo, M. Wholey, An Overview of Superelastic Stent Design.

(Continued)

*Primary Examiner* — Tuan V Nguyen
(74) *Attorney, Agent, or Firm* — Mark J. Kertz, Esq.

(57) ABSTRACT

Systems for treatment of ischemic stroke can include tethered baskets. A basket can be tethered to a pusher or elongate member. A temporary reperfusion device or temporary capture device also can be tethered to the pusher or elongate member.

15 Claims, 35 Drawing Sheets

(56) References Cited

U.S. PATENT DOCUMENTS

| | | | |
|---|---|---|---|
| 5,035,686 A | 7/1991 | Crittenden et al. | |
| 5,057,114 A | 10/1991 | Wittich et al. | |
| 5,222,964 A | 6/1993 | Cooper | |
| 5,222,971 A | 6/1993 | Willard et al. | |
| 5,275,622 A | 1/1994 | Lazarus et al. | |
| 5,312,344 A | 5/1994 | Grinfeld et al. | |
| 5,327,885 A | 7/1994 | Griffith | |
| 5,344,395 A | 9/1994 | Whalen | |
| 5,370,653 A | 12/1994 | Cragg | |
| 5,425,739 A | 6/1995 | Jessen | |
| 5,449,372 A | 9/1995 | Schmaltz | |
| 5,456,667 A | 10/1995 | Ham et al. | |
| 5,527,282 A | 6/1996 | Segal | |
| 5,643,309 A | 7/1997 | Myler et al. | |
| 5,649,906 A | 7/1997 | Gory et al. | |
| 5,653,743 A | 8/1997 | Martin | |
| 5,681,336 A | 10/1997 | Clement et al. | |
| 5,683,449 A | 11/1997 | Marcade | |
| 5,695,469 A | 12/1997 | Segal | |
| 5,718,724 A | 2/1998 | Goicoechea et al. | |
| 5,792,157 A | 8/1998 | Mische | |
| 5,795,322 A | 8/1998 | Boudewijn | |
| 5,800,457 A | 9/1998 | Gelbfish | |
| 5,800,519 A * | 9/1998 | Sandock | 623/1.22 |
| 5,827,324 A | 10/1998 | Cassell et al. | |
| 5,853,419 A | 12/1998 | Imran | |
| 5,916,235 A | 6/1999 | Gugliemlim | |
| 5,922,019 A | 7/1999 | Hankh et al. | |
| 5,928,260 A | 7/1999 | Chin | |
| 5,938,671 A | 8/1999 | Katoh | |
| 5,938,697 A | 8/1999 | Killion et al. | |
| 5,941,895 A | 8/1999 | Myler et al. | |
| 5,941,896 A | 8/1999 | Kerr | |
| 5,947,995 A * | 9/1999 | Samuels | 606/200 |
| 5,951,599 A | 9/1999 | McCrory | |
| 5,961,547 A | 10/1999 | Razavi | |
| 5,968,013 A | 10/1999 | Smith et al. | |
| 5,972,016 A | 10/1999 | Morales | |
| 5,972,019 A | 10/1999 | Engelson | |
| 5,972,219 A | 10/1999 | Habets | |
| 5,976,120 A | 11/1999 | Chow et al. | |
| 5,980,514 A | 11/1999 | Kupiecki et al. | |
| 6,001,118 A | 12/1999 | Daniel et al. | |
| 6,010,449 A | 1/2000 | Selmon et al. | |
| 6,010,498 A | 1/2000 | Guglielmi | |
| 6,010,521 A | 1/2000 | Lee et al. | |
| 6,015,424 A | 1/2000 | Rosenbluth et al. | |
| 6,039,721 A | 3/2000 | Johnson et al. | |
| 6,051,020 A | 4/2000 | Goicoechea et al. | |
| 6,063,070 A | 5/2000 | Eder | |
| 6,063,104 A | 5/2000 | Villar et al. | |
| 6,063,111 A | 5/2000 | Hieshima et al. | |
| 6,066,149 A | 5/2000 | Samson et al. | |
| 6,066,158 A | 5/2000 | Engelson | |
| 6,093,199 A | 7/2000 | Brown et al. | |
| 6,096,034 A | 8/2000 | Kupiecki et al. | |
| 6,106,548 A | 8/2000 | Roubin et al. | |
| 6,117,167 A | 9/2000 | Goicoechea et al. | |
| 6,123,115 A | 9/2000 | Greenhalgh | |
| 6,136,006 A | 10/2000 | Johnson et al. | |
| 6,146,396 A | 11/2000 | Konya et al. | |
| 6,159,238 A | 12/2000 | Killion et al. | |
| 6,159,239 A | 12/2000 | Greenhalgh | |
| 6,164,339 A | 12/2000 | Greenhalgh | |
| 6,168,592 B1 | 1/2001 | Kupiecki et al. | |
| 6,168,604 B1 | 1/2001 | Cano | |
| 6,190,358 B1 | 2/2001 | Fitzmaurice | |
| 6,192,944 B1 | 2/2001 | Greenhalgh | |
| 6,193,708 B1 | 2/2001 | Ken et al. | |
| 6,210,364 B1 | 4/2001 | Anderson | |
| 6,217,609 B1 | 4/2001 | Haverkost | |
| 6,221,096 B1 | 4/2001 | Aiba et al. | |
| 6,231,598 B1 * | 5/2001 | Berry et al. | 623/1.15 |
| 6,238,430 B1 | 5/2001 | Klumb et al. | |
| 6,254,628 B1 | 7/2001 | Wallace et al. | |
| 6,258,115 B1 | 7/2001 | Dubrul | |
| 6,280,413 B1 | 8/2001 | Clark et al. | |
| 6,283,940 B1 | 9/2001 | Mullholland | |
| 6,283,992 B1 | 9/2001 | Hankh et al. | |
| 6,290,720 B1 | 9/2001 | Khosravi et al. | |
| 6,302,906 B1 | 10/2001 | Goicoechea et al. | |
| 6,305,436 B1 | 10/2001 | Andersen et al. | |
| 6,306,141 B1 | 10/2001 | Jervis | |
| 6,322,585 B1 | 11/2001 | Khosravi et al. | |
| 6,325,815 B1 | 12/2001 | Kusleika et al. | |
| 6,325,820 B1 | 12/2001 | Khosravi et al. | |
| 6,325,822 B1 | 12/2001 | Chouinard et al. | |
| 6,344,041 B1 | 2/2002 | Kupiecki et al. | |
| 6,383,205 B1 | 5/2002 | Samson et al. | |
| 6,390,993 B1 | 5/2002 | Cornish et al. | |
| 6,402,771 B1 * | 6/2002 | Palmer et al. | 606/200 |
| 6,454,780 B1 | 9/2002 | Wallace | |
| 6,458,139 B1 * | 10/2002 | Palmer et al. | 606/113 |
| 6,468,301 B1 | 10/2002 | Amplatz et al. | |
| 6,475,236 B1 | 11/2002 | Roubin et al. | |
| 6,475,237 B2 | 11/2002 | Drasler et al. | |
| 6,485,500 B1 | 11/2002 | Kokish | |
| 6,485,509 B2 | 11/2002 | Killion et al. | |
| 6,537,294 B1 | 3/2003 | Boyle et al. | |
| 6,551,341 B2 | 4/2003 | Boylan et al. | |
| 6,551,342 B1 | 4/2003 | Shen et al. | |
| 6,553,810 B2 | 4/2003 | Webb et al. | |
| 6,554,842 B2 | 4/2003 | Heuser et al. | |
| 6,554,856 B1 | 4/2003 | Doorly et al. | |
| 6,558,405 B1 | 5/2003 | McInnes | |
| 6,562,066 B1 | 5/2003 | Martin | |
| 6,569,179 B2 | 5/2003 | Teoh et al. | |
| 6,569,193 B1 | 5/2003 | Cox et al. | |
| 6,575,997 B1 | 6/2003 | Palmer et al. | |
| 6,589,265 B1 | 7/2003 | Palmer et al. | |
| 6,592,607 B1 | 7/2003 | Palmer et al. | |
| 6,592,615 B1 | 7/2003 | Marcade et al. | |
| 6,605,057 B2 | 8/2003 | Fitzmaurice | |
| 6,610,077 B1 | 8/2003 | Hancock et al. | |
| 6,616,617 B1 | 9/2003 | Ferrera et al. | |
| 6,629,953 B1 | 10/2003 | Boyd | |
| 6,632,241 B1 | 10/2003 | Hancock et al. | |
| 6,635,081 B2 | 10/2003 | Khosravi et al. | |
| 6,638,294 B1 | 10/2003 | Palmer | |
| 6,641,590 B1 | 11/2003 | Palmer et al. | |
| 6,652,505 B1 | 11/2003 | Tsugita | |
| 6,652,576 B1 | 11/2003 | Stalker | |
| 6,660,021 B1 | 12/2003 | Palmer et al. | |
| 6,663,607 B2 | 12/2003 | Slaikeu et al. | |
| 6,666,829 B2 | 12/2003 | Cornish et al. | |
| 6,669,723 B2 | 12/2003 | Killion et al. | |
| 6,673,025 B1 | 1/2004 | Richardson et al. | |
| 6,685,722 B1 | 2/2004 | Rosenbluth | |
| 6,685,738 B2 | 2/2004 | Chouinard et al. | |
| 6,695,813 B1 | 2/2004 | Boyle et al. | |
| 6,702,843 B1 | 3/2004 | Brown et al. | |
| 6,709,440 B2 | 3/2004 | Callol et al. | |
| 6,716,178 B1 | 4/2004 | Kilpatrick et al. | |
| 6,723,112 B2 | 4/2004 | Ho et al. | |
| 6,730,104 B1 | 5/2004 | Sepetka et al. | |
| 6,733,519 B2 | 5/2004 | Lashinski | |
| 6,746,468 B1 | 6/2004 | Sepetka et al. | |
| 6,764,506 B2 | 7/2004 | Roubin et al. | |
| 6,773,454 B2 | 8/2004 | Wholey et al. | |
| 6,790,237 B2 | 9/2004 | Stinson | |
| 6,795,979 B2 | 9/2004 | Fournier | |
| 6,802,851 B2 | 10/2004 | Jones et al. | |
| 6,818,015 B2 | 11/2004 | Hankh et al. | |
| 6,821,291 B2 | 11/2004 | Bolea et al. | |
| 6,824,558 B2 | 11/2004 | Parodi | |
| 6,833,003 B2 | 12/2004 | Jones et al. | |
| 6,840,958 B2 | 1/2005 | Nunez et al. | |
| 6,881,220 B2 | 4/2005 | Edwin et al. | |
| 6,893,413 B2 | 5/2005 | Martin | |
| 6,913,612 B2 | 7/2005 | Palmer et al. | |
| 6,949,620 B2 | 9/2005 | Aida et al. | |
| 6,953,472 B2 | 10/2005 | Palmer et al. | |
| 6,955,685 B2 | 10/2005 | Escamilla et al. | |
| 6,960,227 B2 | 11/2005 | Jones et al. | |

(56) References Cited

U.S. PATENT DOCUMENTS

| | | | |
|---|---|---|---|
| 6,991,641 B2 * | 1/2006 | Diaz et al. ................ 606/200 |
| 6,994,723 B1 | 2/2006 | McMahon |
| 7,001,422 B2 | 2/2006 | Escamilla et al. |
| 7,004,954 B1 | 2/2006 | Voss |
| 7,004,955 B2 | 2/2006 | Shen et al. |
| 7,004,956 B2 | 2/2006 | Palmer et al. |
| 7,018,401 B1 | 3/2006 | Hyodoh et al. |
| 7,029,688 B2 | 4/2006 | Hubbell et al. |
| 7,037,329 B2 | 5/2006 | Martin |
| 7,041,116 B2 * | 5/2006 | Goto et al. ................ 606/200 |
| 7,048,014 B2 | 5/2006 | Hyodoh et al. |
| 7,056,328 B2 | 6/2006 | Arnott |
| 7,056,336 B2 | 6/2006 | Armstrong et al. |
| 7,060,091 B2 | 6/2006 | Killion et al. |
| 7,089,218 B1 | 8/2006 | Visel |
| 7,112,217 B1 | 9/2006 | Kugler et al. |
| 7,118,600 B2 | 10/2006 | Dua et al. |
| 7,125,419 B2 | 10/2006 | Sequin et al. |
| 7,128,736 B1 | 10/2006 | Abrams et al. |
| 7,144,421 B2 | 12/2006 | Carpenter et al. |
| 7,147,655 B2 | 12/2006 | Chermoni |
| 7,147,660 B2 | 12/2006 | Chobotov et al. |
| 7,156,869 B1 | 1/2007 | Pacetti |
| 7,160,317 B2 | 1/2007 | McHale |
| 7,169,165 B2 | 1/2007 | Belef et al. |
| 7,172,575 B2 | 2/2007 | El-Nounou |
| 7,172,617 B2 | 2/2007 | Colgan et al. |
| 7,175,607 B2 | 2/2007 | Lim |
| 7,179,273 B1 | 2/2007 | Palmer et al. |
| 7,179,284 B2 | 2/2007 | Khosravi et al. |
| 7,201,769 B2 | 4/2007 | Jones et al. |
| 7,201,770 B2 | 4/2007 | Johnson et al. |
| 7,223,284 B2 | 5/2007 | Khosravi et al. |
| 7,238,197 B2 | 7/2007 | Sequin et al. |
| 7,240,516 B2 | 7/2007 | Pryor |
| 7,241,301 B2 | 7/2007 | Thramann et al. |
| 7,261,727 B2 | 8/2007 | Thielen |
| 7,279,003 B2 | 10/2007 | Berra et al. |
| 7,279,292 B2 | 10/2007 | Imam et al. |
| 7,285,126 B2 | 10/2007 | Sepetka et al. |
| 7,294,147 B2 | 11/2007 | Hartley |
| 7,300,458 B2 | 11/2007 | Henkes et al. |
| 7,306,619 B1 | 12/2007 | Palmer |
| 7,309,345 B2 | 12/2007 | Wallace |
| 7,309,351 B2 | 12/2007 | Escamilla |
| 7,323,000 B2 | 1/2008 | Monstdt et al. |
| 7,323,005 B2 | 1/2008 | Wallace et al. |
| 7,323,006 B2 | 1/2008 | Andreas et al. |
| 7,326,240 B1 | 2/2008 | Caro et al. |
| 7,344,549 B2 | 3/2008 | Boyle et al. |
| 7,344,550 B2 * | 3/2008 | Carrison et al. ........... 606/200 |
| 7,344,556 B2 | 3/2008 | Seguin et al. |
| 7,351,255 B2 | 4/2008 | Andreas |
| 7,354,455 B2 | 4/2008 | Stinson |
| 7,402,169 B2 | 7/2008 | Killion et al. |
| 7,407,509 B2 | 8/2008 | Greenberg et al. |
| 7,435,254 B2 | 10/2008 | Chouinard et al. |
| 7,438,720 B2 | 10/2008 | Shaked |
| 7,455,646 B2 | 11/2008 | Richardson et al. |
| 7,473,272 B2 | 1/2009 | Pryor |
| 7,494,474 B2 | 2/2009 | Richardson et al. |
| 7,549,974 B2 | 6/2009 | Nayak |
| 7,691,122 B2 | 4/2010 | Dieck et al. |
| 7,727,242 B2 | 6/2010 | Sepetka et al. |
| 7,727,243 B2 | 6/2010 | Sepetka et al. |
| 7,749,243 B2 * | 7/2010 | Phung et al. ............... 606/200 |
| 7,780,694 B2 | 8/2010 | Palmer et al. |
| 7,833,240 B2 | 11/2010 | Okushi et al. |
| 7,972,342 B2 | 7/2011 | Gandhi et al. |
| 8,029,530 B2 | 10/2011 | Gesswein et al. |
| 8,052,640 B2 | 11/2011 | Fiorella et al. |
| 8,062,307 B2 | 11/2011 | Sepetka et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,918 B2 | 1/2012 | Gandhi et al. |
| 8,100,935 B2 | 1/2012 | Rosenbluth et al. |
| 8,105,333 B2 | 1/2012 | Sepetka et al. |
| 8,197,493 B2 | 6/2012 | Ferrera et al. |
| 2001/0000797 A1 | 5/2001 | Mazzocchi |
| 2001/0004705 A1 | 6/2001 | Killion et al. |
| 2001/0010013 A1 | 7/2001 | Cox et al. |
| 2001/0031981 A1 | 10/2001 | Evans et al. |
| 2001/0034531 A1 | 10/2001 | Ho et al. |
| 2001/0044633 A1 | 11/2001 | Klint |
| 2001/0044647 A1 | 11/2001 | Pinchuk et al. |
| 2001/0047202 A1 | 11/2001 | Slaikeu et al. |
| 2001/0051823 A1 | 12/2001 | Khosravi et al. |
| 2002/0004667 A1 | 1/2002 | Adams et al. |
| 2002/0004681 A1 | 1/2002 | Teoh et al. |
| 2002/0007210 A1 | 1/2002 | Chouinard et al. |
| 2002/0016564 A1 | 2/2002 | Courtney et al. |
| 2002/0016624 A1 | 2/2002 | Patterson |
| 2002/0032479 A1 | 3/2002 | Hankh et al. |
| 2002/0038142 A1 | 3/2002 | Khosravi et al. |
| 2002/0038146 A1 | 3/2002 | Harry |
| 2002/0052643 A1 | 5/2002 | Wholey et al. |
| 2002/0068968 A1 | 6/2002 | Hupp |
| 2002/0072790 A1 | 6/2002 | McGuckin, Jr. et al. |
| 2002/0087209 A1 | 7/2002 | Edwin et al. |
| 2002/0091355 A1 | 7/2002 | Hayden |
| 2002/0095141 A1 | 7/2002 | Belef |
| 2002/0143387 A1 | 10/2002 | Soetikno et al. |
| 2002/0161377 A1 | 10/2002 | Rabkin |
| 2002/0169458 A1 | 11/2002 | Connors |
| 2002/0183831 A1 | 12/2002 | Rolando et al. |
| 2002/0198588 A1 | 12/2002 | Armstrong et al. |
| 2003/0004536 A1 * | 1/2003 | Boylan et al. ............. 606/200 |
| 2003/0023230 A1 | 1/2003 | Lewis et al. |
| 2003/0023299 A1 | 1/2003 | Amplatz et al. |
| 2003/0032941 A1 | 2/2003 | Boyle |
| 2003/0032977 A1 | 2/2003 | Brady |
| 2003/0040771 A1 | 2/2003 | Hyodoh et al. |
| 2003/0040772 A1 | 2/2003 | Hyodoh et al. |
| 2003/0055440 A1 | 3/2003 | Jones et al. |
| 2003/0055451 A1 | 3/2003 | Jones et al. |
| 2003/0074056 A1 | 4/2003 | Killion et al. |
| 2003/0078605 A1 | 4/2003 | Bashiri et al. |
| 2003/0097114 A1 | 5/2003 | Ouriel et al. |
| 2003/0105484 A1 | 6/2003 | Boyle |
| 2003/0125791 A1 | 7/2003 | Sequin et al. |
| 2003/0125798 A1 | 7/2003 | Martin |
| 2003/0130719 A1 | 7/2003 | Martin |
| 2003/0139796 A1 | 7/2003 | Sequin et al. |
| 2003/0139803 A1 | 7/2003 | Sequin et al. |
| 2003/0149475 A1 | 8/2003 | Hyodoh et al. |
| 2003/0153944 A1 | 8/2003 | Phung et al. |
| 2003/0176914 A1 | 9/2003 | Rabkin et al. |
| 2003/0195554 A1 | 10/2003 | Shen et al. |
| 2003/0199921 A1 | 10/2003 | Palmer et al. |
| 2003/0204202 A1 | 10/2003 | Palmer et al. |
| 2004/0002752 A1 | 1/2004 | Griffin et al. |
| 2004/0006306 A1 | 1/2004 | Evans et al. |
| 2004/0006370 A1 | 1/2004 | Tsugita |
| 2004/0006381 A1 | 1/2004 | Sequin et al. |
| 2004/0019322 A1 | 1/2004 | Hoffmann |
| 2004/0030378 A1 | 2/2004 | Khosravi et al. |
| 2004/0034386 A1 | 2/2004 | Fulton et al. |
| 2004/0039412 A1 | 2/2004 | Isshiki et al. |
| 2004/0049258 A1 | 3/2004 | Khosravi et al. |
| 2004/0054367 A1 | 3/2004 | Jimenez et al. |
| 2004/0059259 A1 | 3/2004 | Cornish et al. |
| 2004/0059407 A1 | 3/2004 | Escamilla et al. |
| 2004/0068288 A1 | 4/2004 | Palmer et al. |
| 2004/0073300 A1 | 4/2004 | Chouinard et al. |
| 2004/0078071 A1 | 4/2004 | Escamilla et al. |
| 2004/0079429 A1 | 4/2004 | Miller et al. |
| 2004/0088002 A1 | 5/2004 | Boyle |
| 2004/0102838 A1 | 5/2004 | Killion et al. |
| 2004/0106979 A1 | 6/2004 | Goicoechea et al. |
| 2004/0114912 A1 | 6/2004 | Okamoto et al. |
| 2004/0117003 A1 | 6/2004 | Ouriel et al. |
| 2004/0147939 A1 | 7/2004 | Rabkin et al. |
| 2004/0153117 A1 | 8/2004 | Clubb et al. |

(56) References Cited

U.S. PATENT DOCUMENTS

| | | |
|---|---|---|
| 2004/0158307 A1 | 8/2004 | Jones et al. |
| 2004/0158312 A1 | 8/2004 | Chouinard et al. |
| 2004/0186562 A1 | 9/2004 | Cox |
| 2004/0193208 A1 | 9/2004 | Talpade et al. |
| 2004/0193246 A1 | 9/2004 | Ferrera |
| 2004/0199201 A1 | 10/2004 | Kellett et al. |
| 2004/0215312 A1 | 10/2004 | Andreas |
| 2004/0215319 A1 | 10/2004 | Berra et al. |
| 2004/0249439 A1 | 12/2004 | Richter et al. |
| 2004/0254628 A1 | 12/2004 | Nazzaro et al. |
| 2004/0260385 A1 | 12/2004 | Jones et al. |
| 2005/0033334 A1 | 2/2005 | Santra et al. |
| 2005/0033349 A1 | 2/2005 | Jones et al. |
| 2005/0033409 A1 | 2/2005 | Burke et al. |
| 2005/0038447 A1* | 2/2005 | Huffmaster ............ 606/200 |
| 2005/0038468 A1 | 2/2005 | Panetta et al. |
| 2005/0038496 A1 | 2/2005 | Jones et al. |
| 2005/0049676 A1 | 3/2005 | Nazzaro et al. |
| 2005/0055047 A1 | 3/2005 | Greenhalgh |
| 2005/0060017 A1 | 3/2005 | Fischell et al. |
| 2005/0075715 A1 | 4/2005 | Borges et al. |
| 2005/0080480 A1 | 4/2005 | Bolea et al. |
| 2005/0090857 A1 | 4/2005 | Kusleika et al. |
| 2005/0090888 A1 | 4/2005 | Hines et al. |
| 2005/0096726 A1 | 5/2005 | Sequin et al. |
| 2005/0102018 A1 | 5/2005 | Carpenter et al. |
| 2005/0107823 A1 | 5/2005 | Leone et al. |
| 2005/0119684 A1 | 6/2005 | Guterman |
| 2005/0125023 A1 | 6/2005 | Bates |
| 2005/0126979 A1 | 6/2005 | Lowe |
| 2005/0131449 A1 | 6/2005 | Salahieh et al. |
| 2005/0131515 A1 | 6/2005 | Cully et al. |
| 2005/0131516 A1 | 6/2005 | Greenhalgh |
| 2005/0159774 A1 | 7/2005 | Belef |
| 2005/0177228 A1 | 8/2005 | Solem et al. |
| 2005/0187612 A1 | 8/2005 | Edwin |
| 2005/0192661 A1 | 9/2005 | Griffen et al. |
| 2005/0209673 A1 | 9/2005 | Shaked |
| 2005/0209675 A1 | 9/2005 | Ton et al. |
| 2005/0209678 A1 | 9/2005 | Henkes et al. |
| 2005/0216050 A1 | 9/2005 | Sepetka et al. |
| 2005/0222583 A1 | 10/2005 | Cano |
| 2005/0222607 A1 | 10/2005 | Palmer et al. |
| 2005/0267570 A1 | 12/2005 | Shadduck |
| 2005/0277978 A1 | 12/2005 | Greenhalgh |
| 2005/0283166 A1* | 12/2005 | Greenhalgh ............ 606/113 |
| 2006/0020285 A1 | 1/2006 | Niermann |
| 2006/0020321 A1 | 1/2006 | Parker |
| 2006/0025845 A1 | 2/2006 | Escamilla et al. |
| 2006/0025850 A1 | 2/2006 | Feller et al. |
| 2006/0030865 A1 | 2/2006 | Balg |
| 2006/0036281 A1 | 2/2006 | Patterson |
| 2006/0052816 A1 | 3/2006 | Bates et al. |
| 2006/0058833 A1 | 3/2006 | VanCamp |
| 2006/0058836 A1 | 3/2006 | Bose et al. |
| 2006/0058838 A1 | 3/2006 | Bose et al. |
| 2006/0074480 A1 | 4/2006 | Bales et al. |
| 2006/0089703 A1 | 4/2006 | Escamilla et al. |
| 2006/0100663 A1 | 5/2006 | Palmer et al. |
| 2006/0106421 A1 | 5/2006 | Teoh |
| 2006/0106448 A1 | 5/2006 | Shaked |
| 2006/0122643 A1 | 6/2006 | Wasicek |
| 2006/0122685 A1 | 6/2006 | Bonsignore et al. |
| 2006/0135947 A1 | 6/2006 | Soltesz et al. |
| 2006/0142841 A1 | 6/2006 | Khosravi et al. |
| 2006/0142849 A1 | 6/2006 | Killion et al. |
| 2006/0195172 A1 | 8/2006 | Luo et al. |
| 2006/0200048 A1 | 9/2006 | Furst |
| 2006/0200221 A1 | 9/2006 | Malewicz |
| 2006/0224180 A1 | 10/2006 | Anderson et al. |
| 2006/0229645 A1 | 10/2006 | Bonnette et al. |
| 2006/0259119 A1 | 11/2006 | Rucker |
| 2006/0265054 A1 | 11/2006 | Greenhalgh et al. |
| 2006/0271090 A1 | 11/2006 | Shaked et al. |
| 2006/0276883 A1 | 12/2006 | Greenberg et al. |
| 2006/0282116 A1 | 12/2006 | Lowe et al. |
| 2006/0287701 A1 | 12/2006 | Pal |
| 2006/0287704 A1 | 12/2006 | Hartley et al. |
| 2007/0032852 A1 | 2/2007 | Machek et al. |
| 2007/0043424 A1 | 2/2007 | Pryor |
| 2007/0043425 A1 | 2/2007 | Hartley et al. |
| 2007/0055299 A1 | 3/2007 | Ishimaru |
| 2007/0055358 A1 | 3/2007 | Krolik et al. |
| 2007/0055360 A1 | 3/2007 | Hanson et al. |
| 2007/0055365 A1 | 3/2007 | Greenberg et al. |
| 2007/0060945 A1 | 3/2007 | Gilson et al. |
| 2007/0067011 A1 | 3/2007 | Krolik et al. |
| 2007/0073376 A1 | 3/2007 | Krolik et al. |
| 2007/0088387 A1 | 4/2007 | Eskridge et al. |
| 2007/0100425 A1 | 5/2007 | Sequin et al. |
| 2007/0118205 A1 | 5/2007 | Davidson et al. |
| 2007/0123972 A1 | 5/2007 | Greenberg et al. |
| 2007/0135826 A1 | 6/2007 | Zaver et al. |
| 2007/0135888 A1 | 6/2007 | Khosravi et al. |
| 2007/0141036 A1 | 6/2007 | Gorrochategui Barrueta et al. |
| 2007/0142896 A1 | 6/2007 | Anderson et al. |
| 2007/0156170 A1 | 7/2007 | Hancock et al. |
| 2007/0156228 A1 | 7/2007 | Majercak et al. |
| 2007/0162109 A1 | 7/2007 | Davila et al. |
| 2007/0191866 A1 | 8/2007 | Palmer et al. |
| 2007/0191884 A1 | 8/2007 | Eskridge et al. |
| 2007/0191924 A1 | 8/2007 | Rudakov |
| 2007/0198028 A1 | 8/2007 | Miloslavski |
| 2007/0198030 A1 | 8/2007 | Martin et al. |
| 2007/0198075 A1 | 8/2007 | Levy |
| 2007/0203452 A1 | 8/2007 | Mehta |
| 2007/0203559 A1 | 8/2007 | Freudenthal et al. |
| 2007/0208367 A1 | 9/2007 | Fiorella et al. |
| 2007/0208371 A1 | 9/2007 | French et al. |
| 2007/0219579 A1 | 9/2007 | Paul |
| 2007/0219621 A1 | 9/2007 | Hartley et al. |
| 2007/0225794 A1 | 9/2007 | Thramann et al. |
| 2007/0233236 A1 | 10/2007 | Pryor |
| 2007/0250040 A1 | 10/2007 | Provost et al. |
| 2007/0266542 A1 | 11/2007 | Melsheimer |
| 2007/0270932 A1 | 11/2007 | Headley et al. |
| 2007/0288034 A1 | 12/2007 | MacCollum et al. |
| 2007/0288037 A1 | 12/2007 | Cheng et al. |
| 2007/0288080 A1 | 12/2007 | Maccollum et al. |
| 2007/0288083 A1 | 12/2007 | Hines |
| 2007/0299503 A1 | 12/2007 | Berra et al. |
| 2008/0001333 A1 | 1/2008 | Kleine et al. |
| 2008/0015558 A1 | 1/2008 | Harlan |
| 2008/0015682 A1 | 1/2008 | Majercak et al. |
| 2008/0033528 A1 | 2/2008 | Satasiya et al. |
| 2008/0039926 A1 | 2/2008 | Majercak et al. |
| 2008/0039930 A1 | 2/2008 | Jones et al. |
| 2008/0045995 A1 | 2/2008 | Guterman et al. |
| 2008/0046064 A1 | 2/2008 | Sequin et al. |
| 2008/0046072 A1 | 2/2008 | Laborde et al. |
| 2008/0051803 A1 | 2/2008 | Monjtadt |
| 2008/0058724 A1 | 3/2008 | Wallace |
| 2008/0071178 A1 | 3/2008 | Greenland et al. |
| 2008/0077175 A1 | 3/2008 | Palmer |
| 2008/0082159 A1 | 4/2008 | Tseng et al. |
| 2008/0086196 A1 | 4/2008 | Truckai et al. |
| 2008/0091231 A1 | 4/2008 | Boyle et al. |
| 2008/0097495 A1 | 4/2008 | Feller et al. |
| 2008/0103477 A1 | 5/2008 | Jones |
| 2008/0103585 A1 | 5/2008 | Monstadt |
| 2008/0109063 A1 | 5/2008 | Hancock et al. |
| 2008/0109067 A1 | 5/2008 | Caro et al. |
| 2008/0114445 A1 | 5/2008 | Melsheimer et al. |
| 2008/0125855 A1 | 5/2008 | Henkes et al. |
| 2008/0140107 A1 | 6/2008 | Bei |
| 2008/0140181 A1 | 6/2008 | Reynolds |
| 2008/0147100 A1 | 6/2008 | Wallace et al. |
| 2008/0161903 A1 | 7/2008 | Sequin et al. |
| 2008/0161936 A1 | 7/2008 | Feller et al. |
| 2008/0167708 A1 | 7/2008 | Molland et al. |
| 2008/0195140 A1 | 8/2008 | Myla |
| 2008/0200946 A1 | 8/2008 | Braun et al. |
| 2008/0208245 A1 | 8/2008 | Hoffman |
| 2008/0208319 A1 | 8/2008 | Rabkin et al. |

(56) References Cited

U.S. PATENT DOCUMENTS

| | | |
|---|---|---|
| 2008/0221554 A1 | 9/2008 | O'Connor et al. |
| 2008/0221600 A1 | 9/2008 | Dieck et al. |
| 2008/0221664 A1 | 9/2008 | Bales et al. |
| 2008/0221671 A1 | 9/2008 | Chouinard et al. |
| 2008/0228216 A1 | 9/2008 | Strauss et al. |
| 2008/0234795 A1 | 9/2008 | Snow et al. |
| 2008/0243229 A1 | 10/2008 | Wallace et al. |
| 2008/0243232 A1 | 10/2008 | Hegg et al. |
| 2008/0247943 A1 | 10/2008 | Lanza et al. |
| 2008/0249598 A1 | 10/2008 | Sherry |
| 2008/0255678 A1 | 10/2008 | Cully et al. |
| 2008/0262506 A1 | 10/2008 | Griffin |
| 2008/0262528 A1 | 10/2008 | Martin |
| 2008/0262532 A1 | 10/2008 | Martin |
| 2008/0262592 A1 | 10/2008 | Jordan et al. |
| 2008/0262952 A1 | 10/2008 | Channell |
| 2008/0269774 A1 | 10/2008 | Garcia et al. |
| 2008/0269868 A1 | 10/2008 | Bei |
| 2008/0275497 A1 | 11/2008 | Palmer et al. |
| 2008/0275498 A1 | 11/2008 | Palmer et al. |
| 2008/0275536 A1 | 11/2008 | Zarins et al. |
| 2008/0281302 A1 | 11/2008 | Murphy et al. |
| 2008/0281350 A1 | 11/2008 | Sepetka et al. |
| 2008/0281393 A1 | 11/2008 | Armstrong et al. |
| 2008/0281397 A1 | 11/2008 | Killion et al. |
| 2008/0281403 A1 | 11/2008 | Kavteladze |
| 2008/0306503 A1 | 12/2008 | Que et al. |
| 2008/0306504 A1 | 12/2008 | Win et al. |
| 2008/0312732 A1 | 12/2008 | Hartley et al. |
| 2008/0319525 A1 | 12/2008 | Tieu et al. |
| 2008/0319533 A1 | 12/2008 | Lehe |
| 2009/0018633 A1 | 1/2009 | Lindquist et al. |
| 2009/0018634 A1 | 1/2009 | State |
| 2009/0018640 A1 | 1/2009 | State |
| 2009/0024157 A1 | 1/2009 | Anukhin |
| 2009/0025820 A1 | 1/2009 | Adams |
| 2009/0030502 A1 | 1/2009 | Sun et al. |
| 2009/0036968 A1 | 2/2009 | Hepworth et al. |
| 2009/0036977 A1 | 2/2009 | Rassat et al. |
| 2009/0062726 A1 | 3/2009 | Ford et al. |
| 2009/0062773 A1 | 3/2009 | Cornish et al. |
| 2009/0062834 A1 | 3/2009 | Moftakhar et al. |
| 2009/0068097 A1 | 3/2009 | Sevrain |
| 2009/0069828 A1 | 3/2009 | Martin et al. |
| 2009/0069836 A1 | 3/2009 | Labdag et al. |
| 2009/0076450 A1 | 3/2009 | Caizza et al. |
| 2009/0082800 A1 | 3/2009 | Janardhan |
| 2009/0093822 A1 | 4/2009 | Ducharme |
| 2009/0105644 A1 | 4/2009 | Leonard et al. |
| 2009/0105722 A1 | 4/2009 | Fulkerson et al. |
| 2009/0105737 A1 | 4/2009 | Fulkerson |
| 2009/0105747 A1 | 4/2009 | Chanduszko et al. |
| 2009/0125053 A1 | 5/2009 | Ferrera et al. |
| 2009/0192455 A1 | 7/2009 | Ferrera et al. |
| 2009/0240213 A1 | 9/2009 | Miyagawa et al. |
| 2009/0240238 A1 | 9/2009 | Grodrian et al. |
| 2009/0292297 A1 | 11/2009 | Ferrera |
| 2009/0299393 A1 | 12/2009 | Martin et al. |
| 2010/0022951 A1 | 1/2010 | Ferrera et al. |
| 2010/0087908 A1 | 4/2010 | Hilaire et al. |
| 2010/0100106 A1 | 4/2010 | Ferrera |
| 2010/0114017 A1 | 5/2010 | Lenker et al. |
| 2010/0114135 A1 | 5/2010 | Wilson et al. |
| 2010/0137892 A1 | 6/2010 | Krolik et al. |
| 2010/0152766 A1 | 6/2010 | Dieck et al. |
| 2010/0174309 A1 | 7/2010 | Fulkerson et al. |
| 2010/0217187 A1 | 8/2010 | Fulkerson et al. |
| 2010/0256600 A1 | 10/2010 | Ferrera |
| 2010/0268264 A1 | 10/2010 | Bonnette |
| 2010/0299911 A1 | 12/2010 | Gianotti et al. |
| 2010/0318097 A1 | 12/2010 | Ferrera et al. |
| 2011/0009875 A1 | 1/2011 | Grandfield et al. |
| 2011/0009941 A1 | 1/2011 | Grandfield et al. |
| 2011/0060212 A1 | 3/2011 | Slee et al. |
| 2011/0152920 A1 | 6/2011 | Eckhouse et al. |
| 2011/0160742 A1 | 6/2011 | Ferrera et al. |
| 2011/0160757 A1 | 6/2011 | Ferrera et al. |
| 2011/0160760 A1 | 6/2011 | Ferrera et al. |
| 2011/0160761 A1 | 6/2011 | Ferrera et al. |
| 2011/0160763 A1 | 6/2011 | Ferrera et al. |
| 2011/0166586 A1 | 7/2011 | Sepetka et al. |
| 2011/0172699 A1 | 7/2011 | Miller et al. |
| 2011/0184456 A1 | 7/2011 | Grandfield et al. |
| 2011/0190797 A1 | 8/2011 | Fulkerson et al. |
| 2011/0202088 A1 | 8/2011 | Eckhouse et al. |
| 2011/0238106 A1 | 9/2011 | Ferrera et al. |
| 2011/0257675 A1 | 10/2011 | Mackiewicz |
| 2011/0270178 A1 | 11/2011 | Fiorella et al. |
| 2011/0288572 A1 | 11/2011 | Martin |
| 2011/0301686 A1 | 12/2011 | Bowman et al. |
| 2011/0319917 A1 | 12/2011 | Ferrera et al. |
| 2012/0016396 A1 | 1/2012 | Dehnad |
| 2012/0016406 A1 | 1/2012 | Ferrera et al. |
| 2012/0022576 A1 | 1/2012 | Ferrera et al. |
| 2012/0022581 A1 | 1/2012 | Wilson et al. |
| 2012/0022634 A1 | 1/2012 | Kusleika et al. |
| 2012/0035648 A1 | 2/2012 | Wilson et al. |
| 2012/0035650 A1 | 2/2012 | Linder et al. |
| 2012/0041411 A1 | 2/2012 | Horton et al. |
| 2012/0041449 A1 | 2/2012 | Eckhouse et al. |
| 2012/0041459 A1 | 2/2012 | Fiorella et al. |
| 2012/0041460 A1 | 2/2012 | Ferrera et al. |
| 2012/0041464 A1 | 2/2012 | Monetti et al. |
| 2012/0041474 A1 | 2/2012 | Eckhouse et al. |
| 2012/0041475 A1 | 2/2012 | Ferrera et al. |
| 2012/0046686 A1 | 2/2012 | Wilson et al. |
| 2012/0065660 A1 | 3/2012 | Ferrera et al. |
| 2012/0071964 A1 | 3/2012 | Cattaneo et al. |
| 2012/0078140 A1 | 3/2012 | Nita |
| 2012/0078285 A1 | 3/2012 | Griffin |
| 2012/0089216 A1 | 4/2012 | Rapaport et al. |
| 2012/0116443 A1 | 5/2012 | Ferrera et al. |
| 2012/0265238 A1 | 10/2012 | Hopkins et al. |

FOREIGN PATENT DOCUMENTS

| | | |
|---|---|---|
| EP | 1000590 | 5/2000 |
| EP | 1437097 | 7/2004 |
| EP | 2257248 B1 | 10/2011 |
| EP | 2301450 B1 | 11/2011 |
| EP | 2417919 A2 | 2/2012 |
| JP | 2003-033359 A | 2/2003 |
| JP | 2006-094876 A | 4/2006 |
| JP | 2007-222658 A | 9/2007 |
| JP | 2007-236471 A | 9/2007 |
| WO | WO-94/03127 A1 | 2/1994 |
| WO | WO98/55173 | 12/1998 |
| WO | WO-99/44542 A2 | 9/1999 |
| WO | WO00/32265 | 6/2000 |
| WO | WO00/53120 | 9/2000 |
| WO | WO-01/08743 | 2/2001 |
| WO | WO01/36034 | 5/2001 |
| WO | WO01/45569 | 6/2001 |
| WO | WO03/011188 | 2/2003 |
| WO | WO03/017823 | 3/2003 |
| WO | WO 2007/089897 | 8/2007 |
| WO | WO2007/121005 | 10/2007 |
| WO | WO 2008/117256 A2 | 10/2008 |
| WO | WO 2008/117257 A2 | 10/2008 |
| WO | WO-2008/124728 | 10/2008 |
| WO | WO2009/105710 | 8/2009 |
| WO | WO2009/124288 | 10/2009 |
| WO | WO2009/126747 | 10/2009 |
| WO | WO2010/010545 | 1/2010 |
| WO | WO2010/023671 | 3/2010 |
| WO | WO2010/046897 | 4/2010 |
| WO | WO2010/049121 | 5/2010 |
| WO | WO2010/062363 | 6/2010 |
| WO | WO2010/102307 | 9/2010 |
| WO | WO2010/115642 | 10/2010 |
| WO | WO-2010/121037 | 10/2010 |
| WO | WO-2010/121049 A9 | 12/2010 |
| WO | WO-2011/054531 A3 | 7/2011 |
| WO | WO-2011/095352 | 8/2011 |

(56) References Cited

FOREIGN PATENT DOCUMENTS

| WO | WO-2011/133486 | 10/2011 |
|----|----|----|
| WO | WO-2011/135556 | 11/2011 |
| WO | WO-2011/144336 | 11/2011 |
| WO | WO-2011/147567 | 12/2011 |
| WO | WO-2012/009675 A2 | 1/2012 |
| WO | WO-2012/025245 | 3/2012 |
| WO | WO-2012/025247 | 3/2012 |

OTHER PUBLICATIONS

Michael E. Kelly, MD, et al., Recanalization of an Acute Middle Cerebral Artery Occlusion Using a Self-Expanding, Reconstrainable, Intracranial Microstent as a Temporary Endovascular Bypass; Stroke, Jun. 2008, pp. 1770-1773, vol. 39, issue 6, United States.

Eric Sauvegeau, MD et al., Middle Cerebral Artery Stenting for Acute Ischemic Stroke After Unsuccessful Merci Retrieval; Neurosurgery (Special Technical Report), Apr. 2007, pp. 701-706, vol. 60, issue 4, United States.

David M. Pelz, et al., Advances in Interventional Neuroradiology 2007; Stroke, Jan. 2008, pp. 268-272, vol. 39, issue 1, United States.

Philippa C. Lavallee, et al., Stent-Assisted Endovascular Thrombolysis Versus Intravenous Thrombolysis in Internal Carotid Artery Dissection with Tandem Internal Carotid and Middle Cerebral Artery Occlusion; Stroke, Aug. 2007, pp. 2270-2274, vol. 38, issue 8, United States.

E.I. Levy et al., Self-Expanding Stents for Recanalization of Acute Cerebrovascular Occlusions; AJNR, May 2007, pp. 816-822, vol. 28, United States.

Micro Therapeutics, Inc., DBA EV3 Neurovascular, Inc., Solitaire FR Revascularization Device, Instructions for Use, 70494-001 Rev. Mar. 2009.

Micro Therapeutics, Inc., DBA EV3 Neurovascular, Inc., Fully deployable. Completely retrievable. Solitaire AB, Neurovascular Remodeling Device.

Robertson, Kathy, Stroke device startup lands National Science Foundation grant, Sacramento Business Journal, Oct. 23, 2009, Sacramento, California, USA.

Henkes, H. et al., "A Microcatheter-Delivered Highly-Flexible and Fully-Retrievable Stent, Specifically Designed for Intracranial Use," *Interventional Neuroradiology*, vol. 9, pp. 391-393 (Dec. 2003).

Doerfler, A. et al., "A Novel Flexible, Retrievable Endovascular Stent System for Small-Vessel Anatomy: Preliminary In Vivo Data," *Am. J. Neuroradiol.* vol. 26, pp. 862-868 (Apr. 2005).

Liebig, T. et al., "A novel self-expanding fully retrievable intracranial stent (SOLO): experience in nine procedures of stent-assisted aneurysm coil occlusion," *Neuroradiology* vol. 48, pp. 471-478 (Jul. 2006).

Yavuz, K. et al., "Immediate and midterm follow-up results of using an electrodetachable, fully retrievable SOLO stent system in the endovascular coil occlusion of wide-necked cerebral aneurysms," J. Neurosurg. vol. 107, pp. 49-55 (Jul. 2007).

"Penumbra, Inc. Enrolls First Patients in Pulse Clinical Trial to Evaluate a Fully Retrievable, Dense Mesh Temporary Stent for Immediate Flow Restoration in Interventional Acute Ischemic Stroke Treatment," Business Wire, Nov. 1, 2010, downloaded at http://www.businesswire.com/news/home/20101101006991/en/Penumbra-Enrolls-Patients-PULSE-Clinical-Trial-Evaluate.

U.S. Appl. No. 60/980,736, filed Oct. 17, 2007, Fulkerson et al.
U.S. Appl. No. 60/987,384, filed Nov. 12, 2007, Fulkerson et al.
U.S. Appl. No. 61/015,154, filed Dec. 19, 2007, Ferrera et al.
U.S. Appl. No. 61/057,613, filed May 30, 2008, Ferrera et al.
Wakhloo, et al., "Retrievable Closed Cell Intracranial Stent for Foreign Body and Clot Removal," Neurosurgery, May 2008.

\* cited by examiner

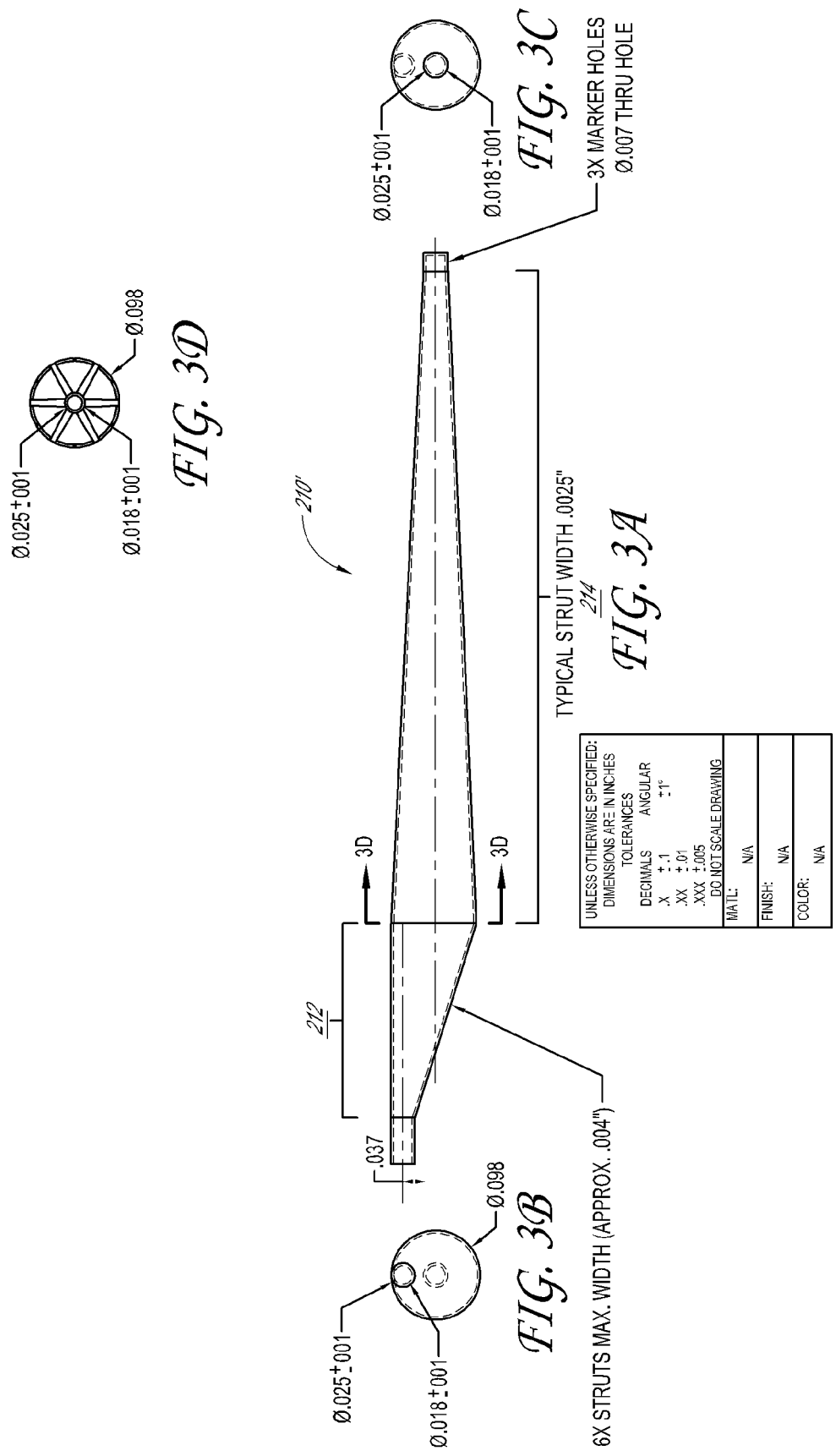

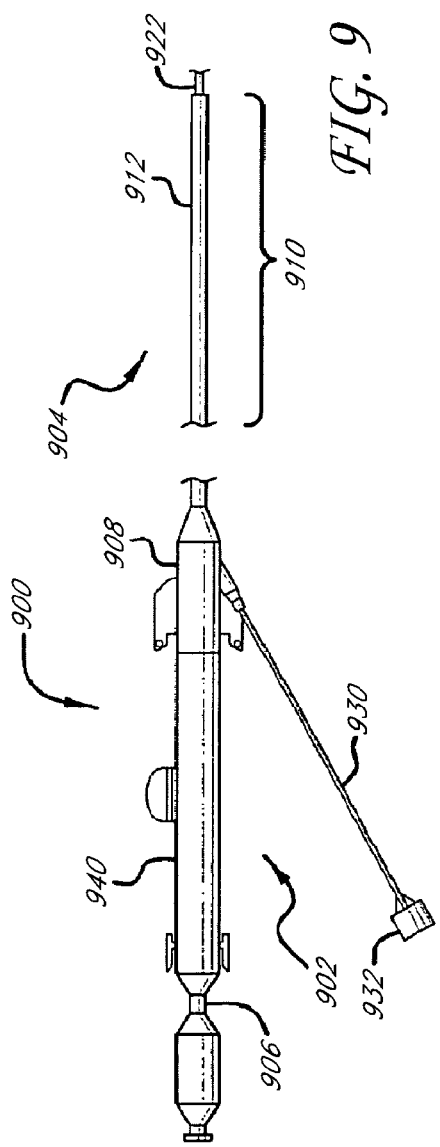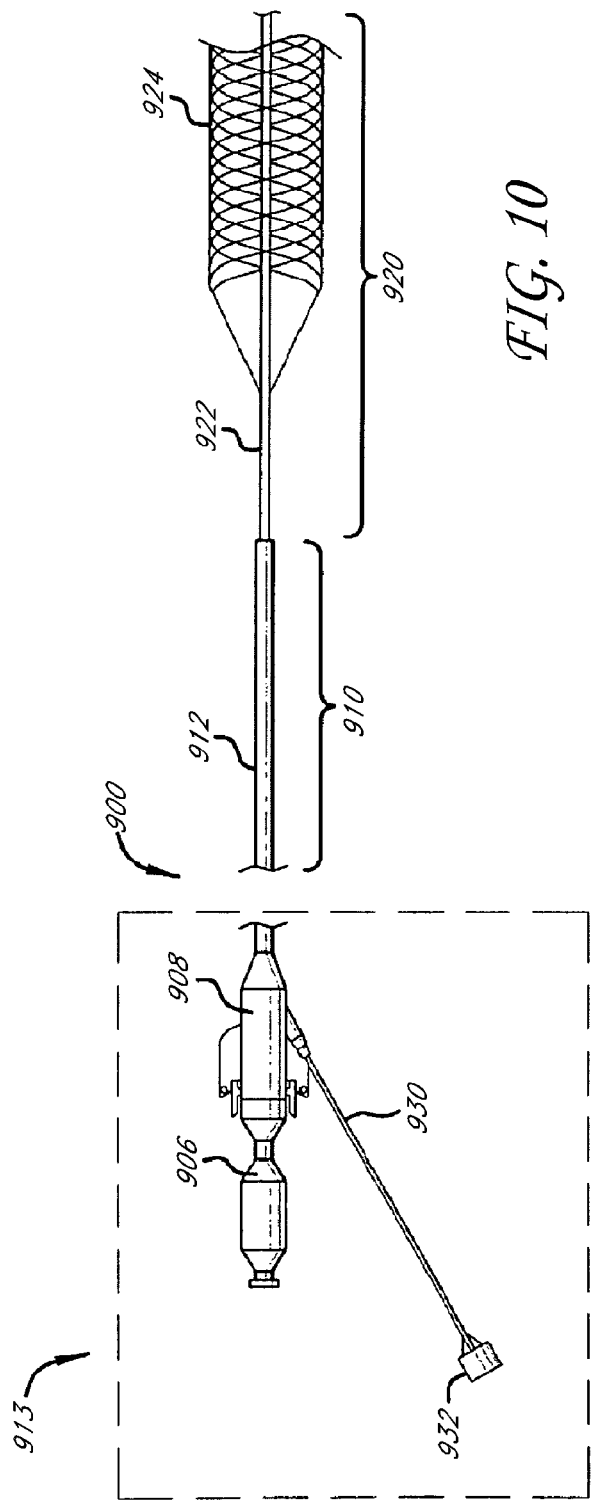

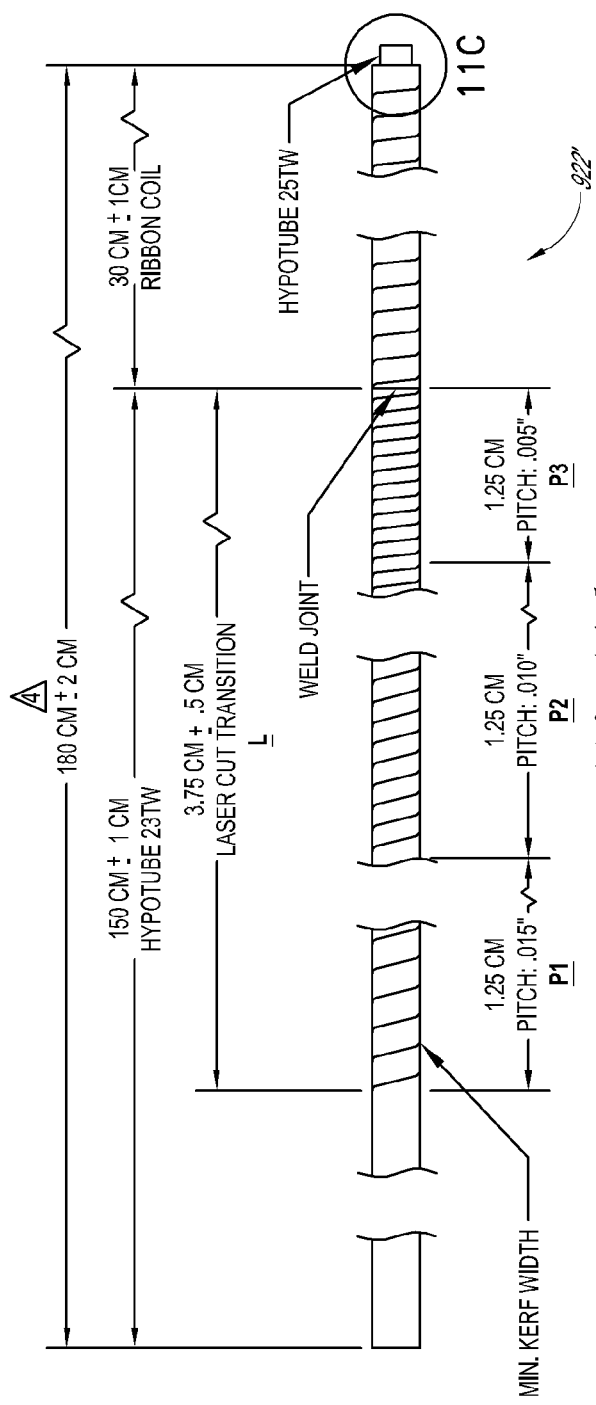
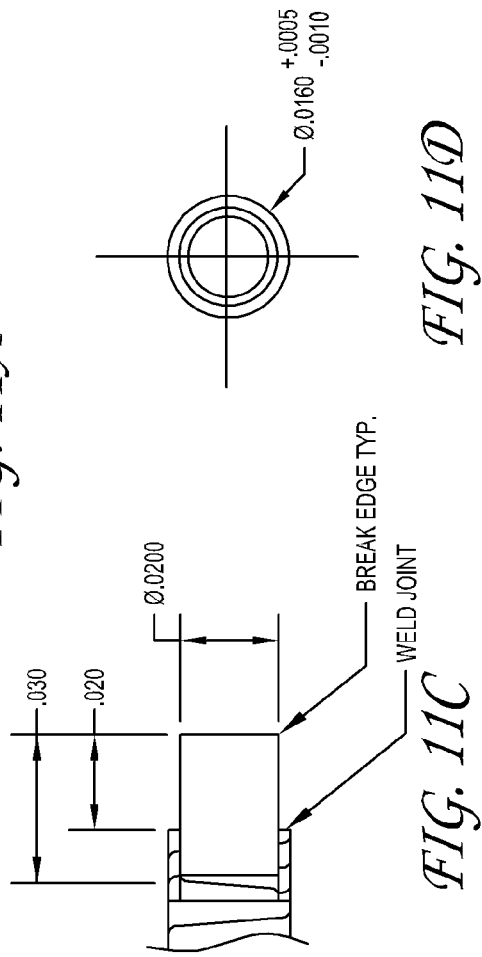
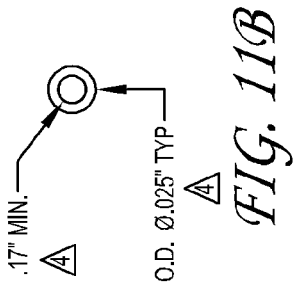

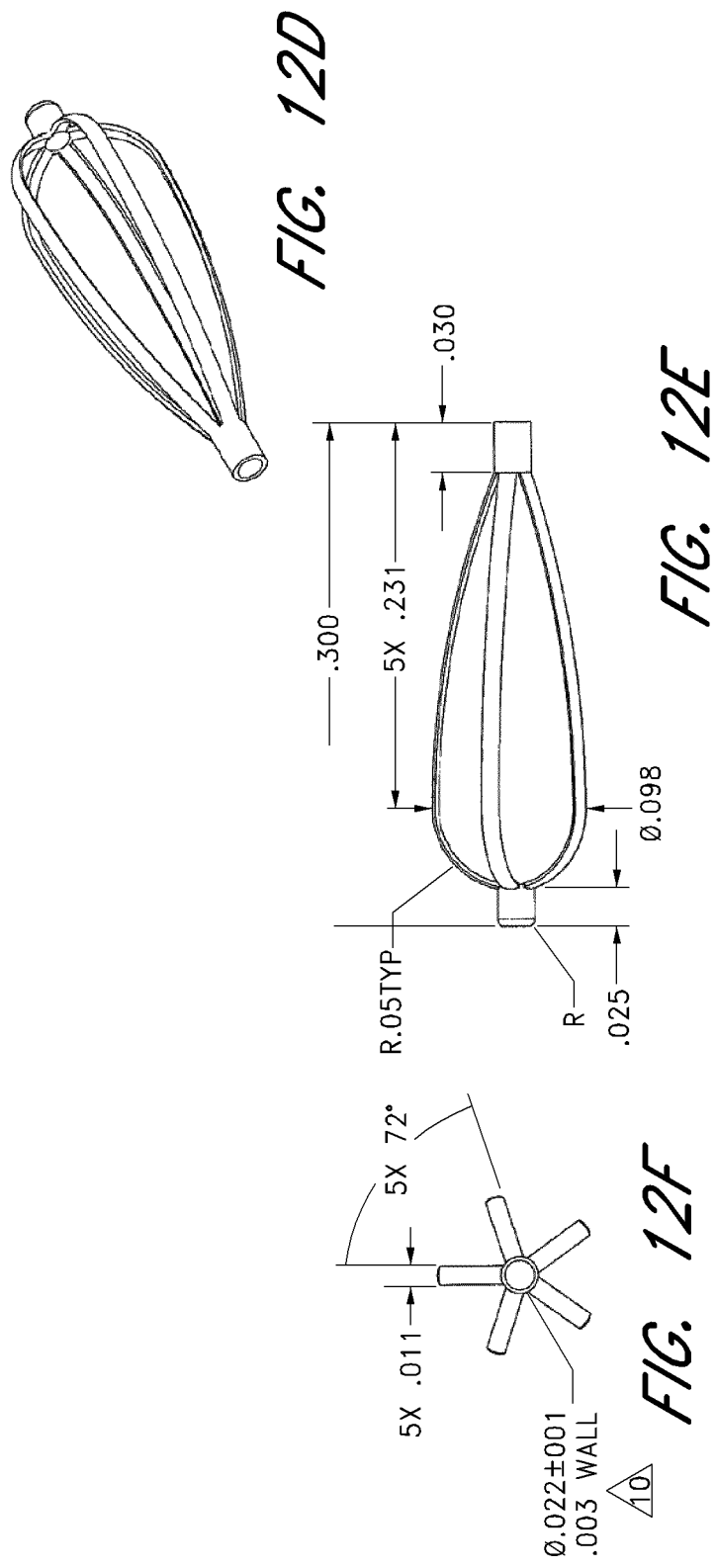

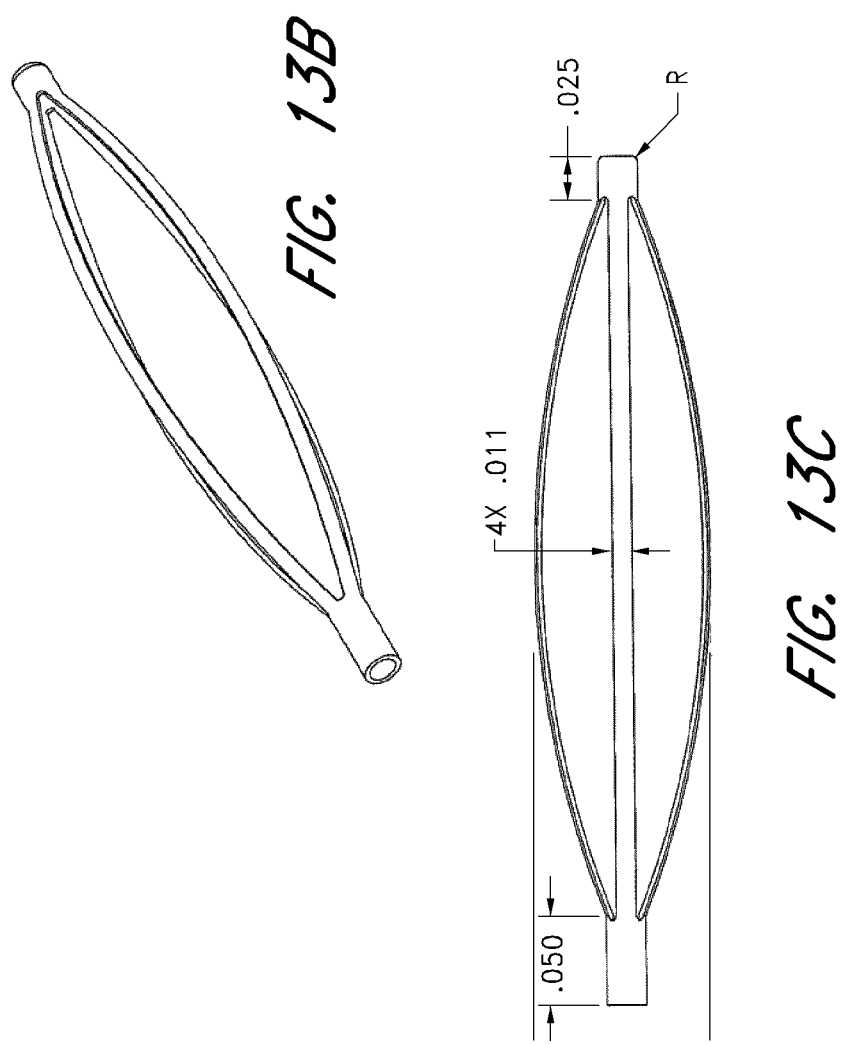

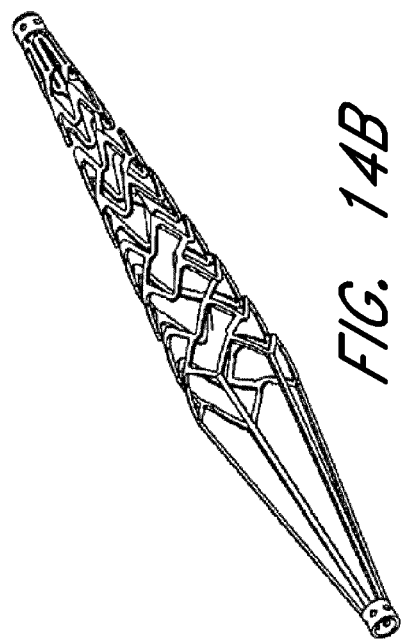
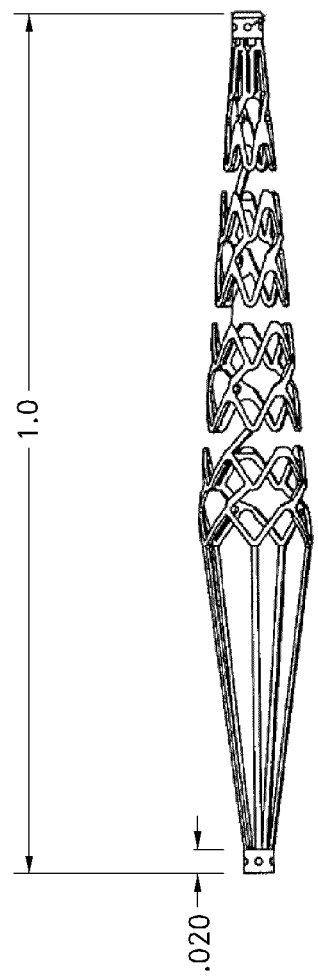

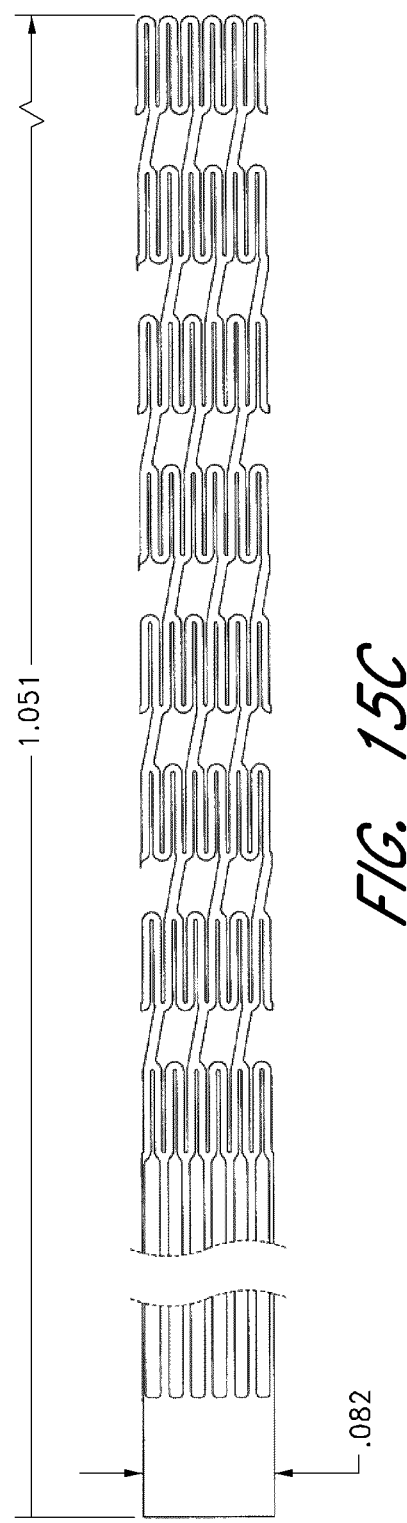

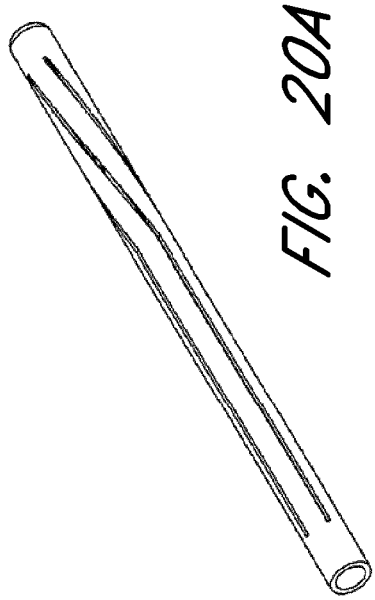
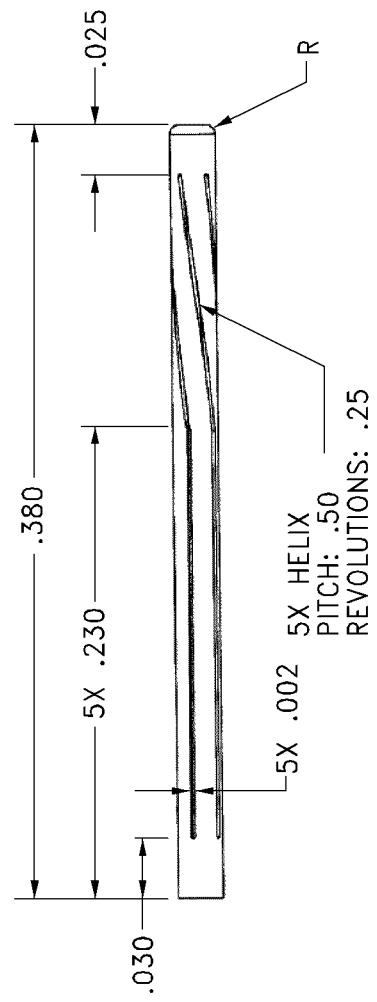
FIG. 20A
FIG. 20B
FIG. 20C

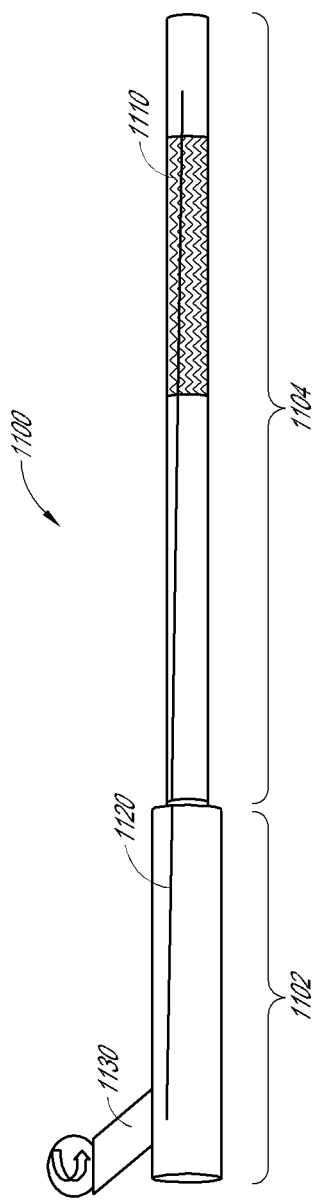
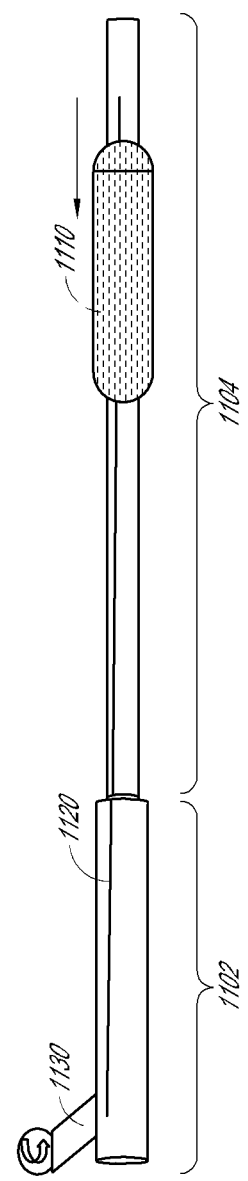
FIG. 21A
FIG. 21B

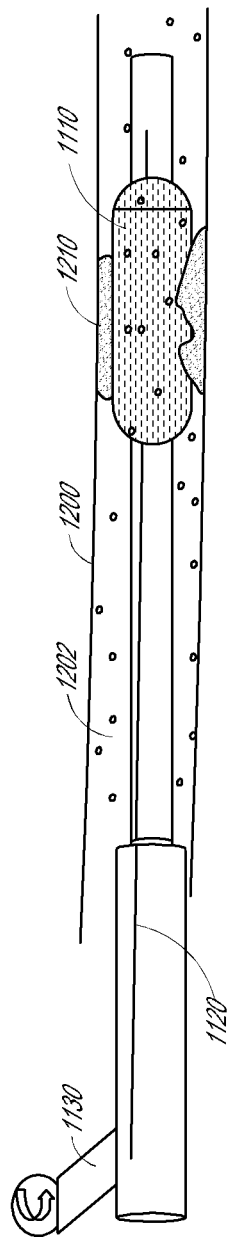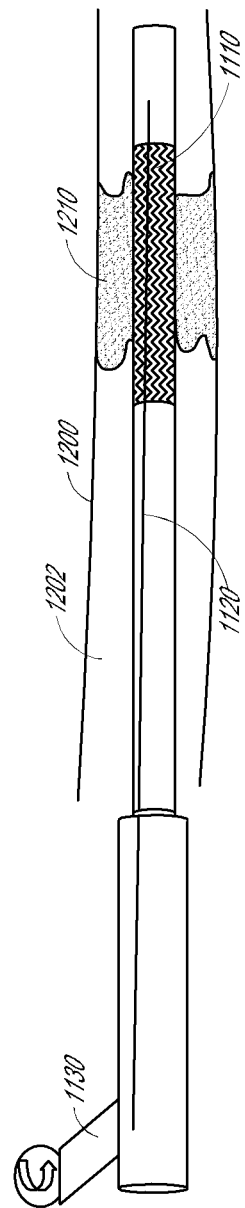
FIG. 22A
FIG. 22B

EMBOLUS REMOVAL SYSTEMS WITH BASKETS

RELATED APPLICATIONS

This application claims the Paris Convention Priority of and fully incorporates by reference, U.S. Provisional Application Ser. No. 60/980,736, filed on Oct. 17, 2007; Application Ser. No. 60/987,384, filed on Nov. 12, 2007; Application Ser. No. 61/015,154, filed on Dec. 19, 2007; Application Ser. No. 61/044,392, filed on Apr. 11, 2008; Application Ser. No. 61/057,613, filed on May 30, 2008; and U.S. Utility application Ser. No. 12/123,390, filed on May 19, 2008 by the present and the instant assignee.

BACKGROUND OF THE INVENTION

The present invention relates to minimally invasive and catheter delivered embolic capture devices for use in the vasculature, especially those suited for usage in the brain and vessel systems perfusing the same.

Several acute stroke therapy trials were reported in 2007. Interventional Management of Stroke (IMS) II found a 9.9% rate of symptomatic intracerebral hemorrhage after combination IV-intra-arterial (IA) tissue-type plasminogen activator therapy was administered within 3 hours of acute stroke onset.

Further results from the MERCI and Multi-MERCI investigators have shown that successful recanalization of acute distal ICA and proximal middle cerebral artery occlusions can be achieved in 53% to 63% of patients using the MERCI retriever (Concentric Medical) alone or in combination with IV/IA thrombolytics, yet symptomatic hemorrhages occurred in 6% of those patients who were recanalized.

Another approach in those who fail MERCI retrieval has been to use angioplasty or self-expanding stents to compress friable clots and allow better penetration of thrombolytic agents. Recanalization rates of up to 89% with balloons and 79% with stents have been achieved in small numbers of patients.

Reports of aggressive revascularization of acute ICA and tandem ICA/middle cerebral artery occlusions using stents and intracranial thrombolysis have demonstrated the feasibility of this approach, again in small numbers of patients.

Attempts to identify prognostic factors for hemorrhagic complications and eventual clinical outcomes in patients undergoing these aggressive multimodal interventions showed that residual distal occlusions, tandem occlusions, larger initial pretreatment CT infarct size by Alberta Stroke Program Early CT Score (ASPECTS) score, hyperglycemia and use of both IA and IV thrombolytics were all associated with negative results. Novel mechanical revascularization strategies used deflated microballoon catheters and the Alligator retrieval device (Chestnut Medical Technologies) to open vessels that may be refractory to IA thrombolytics or the MERCI device.

There are new stents being used to assist in the coiling of wide-necked aneurysms, such as the closed-cell design Enterprise (Cordis Neurovascular, Inc), the electrodetachable, fully retrievable Solo (eV3 Neurovascular) and the covered, balloon-expandable Willis (Microport). Development of significant focal stenosis remains a problem, seen in up to 5.8% of stent-assisted cases. A novel approach is to use a high-coverage, endoluminal mesh to divert flow and thus induce aneurysm thrombosis. The Pipeline Neuroendovascular Device (Chestnut Medical Technologies) is a tubular, bimetallic implant with approximately 30% coverage by area. Preliminary experience in humans has been encouraging.

It is hoped that immunohistochemical and molecular biological data can be used to develop biologically active endovascular devices in the future. A novel method for depositing viable, migration capable fibroblasts on coils and successfully passing them through microcatheters may be a promising technique for endovascular intervention.

Intra-arterial (IA) therapies for acute stroke have evolved over the past decade. Despite the promising results of the PROACT II study, which demonstrated a 66% recanalization rate, substantially higher recanalization rates with IA pharmacologic thrombolysis have not been achieved over the past 7 years. The Food and Drug Administration recently approved a clot retrieval device (Merci retriever X5, X6; Concentric Medical, Mountain View, Calif.). Unfortunately, when used alone, the clot retriever is successful in only approximately 50% of cases, and multiple passes with this device are often required to achieve successful recanalization. IA thrombolytics administered concomitantly enhance the procedural success of this device but may increase the risk of hemorrhagic transformation of the reperfused infarction. There have been several reports of coronary stent implantation used for mechanical thrombolysis of recalcitrant occlusions. In a recent report, stent placement with balloon-mounted or self-expanding coronary stents was shown to be an independent predictor for recanalization of both intracranial and extracranial cerebrovascular occlusions. In another recent report, recanalization rates of 79% were achieved using balloon-mounted stent technology.

Self-expanding stents designed specifically for the cerebrovasculature can be delivered to target areas of intracranial stenosis with a success rate of >95% and an increased safety profile of deliverability because these stents are deployed at significantly lower pressures than balloon-mounted coronary stents. There has been an anecdotal report of the use of a self-expanding stent in the setting of acute symptomatic intracranial occlusion. In addition, a recent comparison of self-expanding and balloon-mounted stents in an animal model of acute embolic occlusion has shown no difference in the 2 stent groups with respect to recanalization rates.

This retrospective multicenter series demonstrates that the use of self-expanding stents is feasible in the setting of symptomatic medium- and large-vessel intracranial occlusions. With stent placement as a first-line mechanical treatment or as a "last-resort" maneuver, TIMI/TICI 2 or 3 revascularization was successfully obtained in 79% of the lesions in which stents were placed. This retrospective review suggests that focal occlusions limited to a single medium or large vessel, particularly solitary occlusions of the MCA or VBS, may be preferentially amenable to stent placement and thus can help clinicians to achieve improved rates of recanalization. In addition, gender may play a role in the success of self-expanding stent implantation: TIMI/TICI 2 or 3 flow was documented in all female patients studied, and female patients were more likely to achieve improved clinical outcomes as measured by NIHSS and mRS scores. Most importantly, our preliminary experience may lead to future pivotal studies that might aid clinicians to better stratify patients most likely to derive maximal clinical benefit from stent placement.

The use of other mechanical means has been reported to be effective in recanalization of acute occlusions. In the MERCI trial, overall recanalization rates (TIMI/TICI 2 or 3 flow) of 48% were achieved with the Merci mechanical clot retriever.

Several authors have proposed endovascular treatment with stent deployment for ICA dissection with high-grade stenosis or occlusion when anticoagulation fails to prevent a new ischemic event. In these cases, the MCA was patent.

We found that stent-assisted endovascular thrombolysis/thrombectomy compared favorably with IV rtPA thrombolysis.

This higher rate of MCA recanalization could be explained by carotid flow restoration, allowing direct access to the MCA thrombus.

Endovascular treatment could potentially extend the therapeutic window beyond 3 hours. Actually, in all cases in the endovascular group, MCA recanalization was obtained by 291 minutes.

Despite these promising preliminary results, potential drawbacks related to the procedure must be considered. Acute complications such as transient ischemic attack, ischemic stroke, femoral or carotid dissection, and death have been reported. Other potential hazards of endovascular treatment of carotid dissection could be observed, as they were in stenting of other cases of arteriopathy. In our series, 1 embolic stroke and 1 acute in-stent thrombosis occurred in the same patient. Despite this new infarction, we observed significant neurologic improvement in this patient, probably because the MCA remained patent. Late stent thrombosis has also been reported.

SUMMARY OF THE INVENTION

Devices, methods, and systems facilitate and enable treatment of ischemic or hemorrhagic stroke. More specifically, a tethered basket-like system operates in conjunction with a microcatheter system, to provide arterial support and capture emboli.

According to a feature of the present invention, a device for the removal of emboli is disclosed comprising a mesh capturer having at least an undeployed state and a deployed state, the mesh capturer being inserted into the neurovasculature in an undeployed state and removed from the microvasculature in its deployed state; wherein the mesh capturer is deployed into its deployed state distal to an embolus and advanced proximally until the embolus is substantially contained within the mesh capturer; and wherein the basket is deployed above the subclavian artery and common carotid artery.

According to a feature of the present invention, a method for removing an embolus is disclosed comprising inserting a microcatheter and guidewire distal to an embolus; inserting a embolus capture device over the wire through the microcatheter distal to the embolus; deploying the embolus capture device; retracting the deployed embolus capture device until the embolus is substantially contained within the embolus capture device; and removing the embolus capture device.

BRIEF DESCRIPTION OF THE FIGURES

The above-mentioned features and objects of the present invention will become more apparent with reference to the following description taken in conjunction with the accompanying drawings wherein like reference numerals denote like elements and in which:

FIGS. 3A-3D illustrate a side, front, back and section view, respectively of an embodiment of an offset clot basket;

FIG. 9 is a perspective view of an embodiment of an acute stroke recanalization system according to embodiments of the present disclosure in a first configuration;

FIG. 10 is a perspective view of an embodiment of an acute stroke recanalization system according to embodiments of the present disclosure tailored for use with the neurovasculature in a second configuration, further illustrating modular aspects of the system as used with tethered or reconstrainable self-expanding neurological medical devices;

FIG. 11A-11D illustrate an embodiment of an inner catheter of the acute stroke recanalization system of FIGS. 9 and 10;

FIGS. 12A-12F, 13A-13C, 14A-14D, 15A-15D, 16A-16C, 17A-17C, 18, 19, and 20A-20F illustrate various embodiments of revascularization and/or embolus removal devices;

FIGS. 21A and 21B are perspective views of an embodiment of a rapid reperfusion device of the present disclosure;

FIGS. 22A and 22B are perspective views of an embodiment of a method for use of a rapid reperfusion device of the present disclosure;

DETAILED DESCRIPTION OF THE INSTANT TEACHINGS

Figure 1:
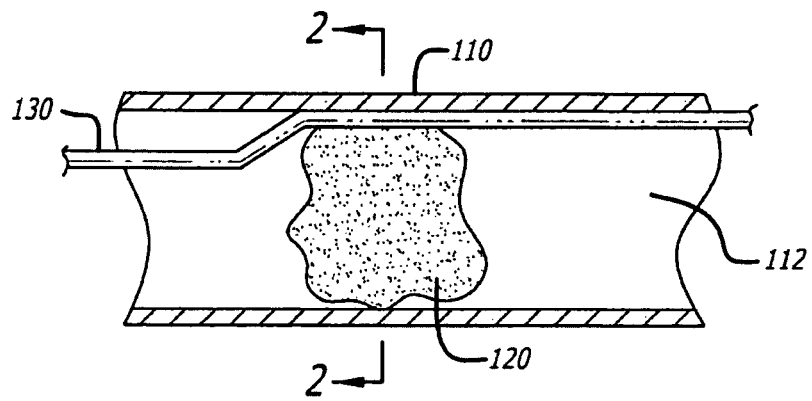
FIG. 1 shows a side view schematic of a microcatheter with wire passing an embolus.

In the following detailed description of embodiments of the invention, reference is made to the accompanying drawings in which like references indicate similar elements, and in which is shown by way of illustration specific embodiments in which the invention may be practiced. These embodiments are described in sufficient detail to enable those skilled in the art to practice the invention, and it is to be understood that other embodiments may be utilized and that logical, mechanical, biological, electrical, functional, and other changes may be made without departing from the scope of the present invention. The following detailed description is, therefore, not to be taken in a limiting sense, and the scope of the present invention is defined only by the appended claims. As used in the present invention, the term "or" shall be understood to be defined as a logical disjunction and shall not indicate an exclusive disjunction unless expressly indicated as such or notated as "xor."

The ideal stent for intracranial use would be flexible, precisely delivered, retrievable, able to be repositioned, atraumatic, available in various lengths and diameters, thin-walled and radiopaque. It should provide sufficient coverage to restrain coils, while having wide enough fenestrations to permit catheterisation with coil or other embolic agent delivery catheters. The currently available over-the-wire stents are not ideal. The balloon-expandable stents of sufficient length are too stiff to be reliably and safely deployed. While existing self-expanding stents offer some improvement in this respect there are still serious difficulties in deploying them in distal locations and the currently available or planned stents for intracranial use are not available in the small diameters necessary for distal intracranial use.

The stent is delivered through a micro-catheter, allowing standard microcatheter/wire techniques to reach locations inaccessible to over-the-wire stents. It fulfills all the criteria mentioned above. A particularly appealing characteristic is its ability to be retrieved and repositioned after complete delivery, if its position is felt to be suboptimal or if the stent proves not to be necessary. The stent conforms completely to the normal vessel geometry and is not prone to strut opening on convexities. It is compatible with all currently used embolic agents for aneurysm occlusion and is MR compatible.

Stents have been used widely in occlusive lesions in the peripheral, renal, and coronary arteries to treat stenosis of vessels narrowed by a variety of pathologic conditions. Initially used mainly in extracranial cerebral vessels for carotid artery stenosis or the treatment of pseudoaneurysms of the extracranial carotid artery, small stents are now increasingly used for intracranial vessel disease such as the treatment of wide-necked aneurysms not amenable to conventional endovascular techniques.

Major limitations of the currently available stents, usually cardiac stents, however, are their relative stiffness, rendering them not flexible enough to pass the C1/C2 vertebral artery or carotid siphon tortuosities.

The design constraints for the device used in this study were to develop an endovascular stent that is flexible enough to be delivered via a microcatheter and to be placed in small vessels but with sufficient radial forces to conform to the vessel wall when deployed.

Leaving the guidewire in place after stent deployment in curved vessels might be an option to stabilize the stent and thus prevent stent displacement while catheterizing the aneurysm with a second microcatheter. In contrast to the Neuroform, because of the design of our stent, displacement should not be an issue.

The present inventors have realized that by leveraging a conventional self-expanding reperfusion device delivery platform, a poly-modic system can be iterated which crosses a embolus, filters, and either removes the offending embolus or is optionally emplaced to address the same. A paucity of extant systems effective for such combination therapies is noted among the art. The instant system allows for natural lysis, perfusion of the challenged vessels, and importantly filters any particulates generated, to obviate the need to be concerned with distal migration of the particulates generated.

The present invention relates to emboli removal devices used to treat, among other things, ischemic stroke. Naturally, therefore, the emboli removal devices of the present invention are designed to be used in neuro-type applications, wherein the specifications of the present catheters and emboli removal devices may be deployed in the blood vessels of the cerebral vascular system. Similarly contemplated for the emboli removal systems and catheters of the present invention is deployment in other parts of the body wherein the specifications of the present invention may be used in other vessels of the body in a non-invasive manner. Specifically, the inventors of the present invention have devised devices and methods of the removal of neurocranial emboli without causing distal complication arising from the passing of larger pieces of a recovered embolus distal to the location of the original embolus.

According to embodiments, disclosed herein is a catheter-emboli removal system. The emboli removal devices of the present invention are for reperfusion of blood vessels. When the catheter-emboli removal system of the present invention is deployed into a blood vessel having an embolus, the emboli removal device is expanded and moved proximally along the vessel so that the embolus is substantially contained with the mesh basket of the emboli removal device.

According to the instant teachings, deployment of the system of the present invention establishes immediate 50% of the diameter of the lumen patency of the vessel being addressed by removing the embolus occluding the vessel. Among the prior art, no system having adequately small profile with flexibility to promote improved access for in-site treatment is known which may be used as a temporary (not implanted) solution and removed without substantial damage to the vasculature.

Additionally, in reperfusion applications the emboli removal device may be deployed as a safety device. As the embolus lyses, the deployed emboli removal device filters larger embolus particles from migrating distally, thereby reducing the chances of further complications. If reperfusion is unsuccessful, then the emboli removal device is retracted proximally, thereby substantially capturing the embolus. Then the entire device is removed together with the micro-catheter.

Figure 2:
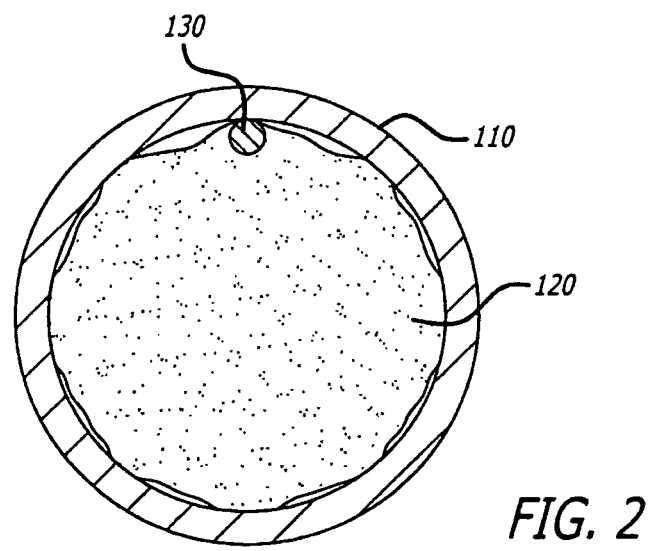
FIG. 2 shows a cross-sectional schematic of an embodiment of a microcatheter wire passing by an embolus at a point of least resistance.

According to embodiments and as illustrated in FIG. 1, a cross sectional view of an artery 110 having embolus 120 in artery lumen 112 is shown. Guidewire 130 inserted through a thrombus tends to follow the path of least resistance through the softest parts of embolus 120. When a microcatheter is inserted along guidewire 130, it likewise follows this path of least resistance. Accordingly, when a stent or embolus capture device is inserted via guidewire 130, it is deployed offset because guidewire 130 is not centered in the vessel in many cases, as illustrated in FIG. 2. Those skilled understand how struts of the line subject devices enable recapturability, flexibility and tracking.

To address the problem of the guidewire offset, the inventors devised an embolus capture device or basket 200 that is adept at capturing embolus 120 even when deployed in an offset way. As part of the embolus capture device/basket 200 design, pieces of embolus 120 that break away from embolus 120 are recaptured to prevent potential migration more distal in the vasculature which may potentially cause other emboli, too remote to safely address.

Figure 3:
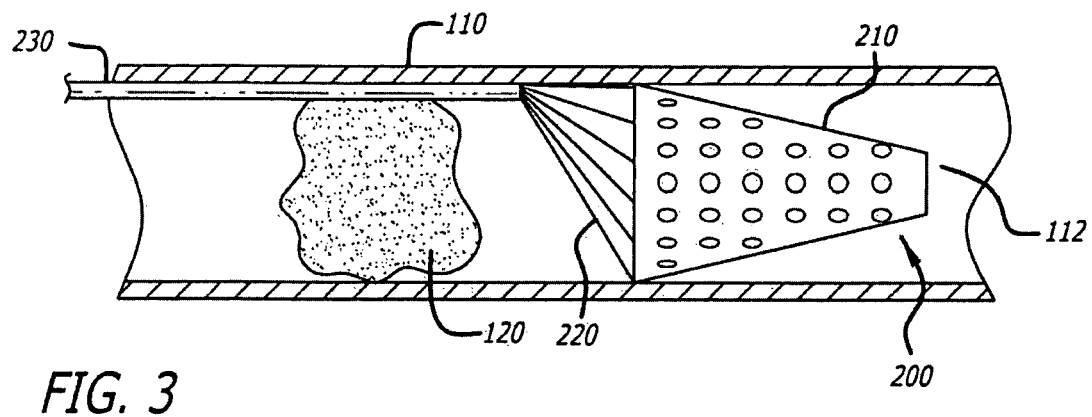
FIG. 3 is a side view of an embodiment of a device for capturing emboli according to the present invention comprising a basket for capturing the embolus.

As illustrated in FIG. 3, blood vessel 110 is shown having vessel lumen 112 and embolus 120. As illustrated, embolus capture device/basket 200 is deployed for capture of embolus 120. As illustrated, embolus capture device/basket 200 is deployed along an offset guidewire. However, embolus capture device 200 is designed for offset deployment to deploy such that it occupies about the center of vessel 110, which ensure maximum efficiency in the capture of embolus 120. It will be readily recognized that the devices of the present invention need not be deployed offset.

Embolus capture device/basket 200 comprises mesh basket 210 and tethers 220 which are deployed from microcatheter 230. Mesh basket 210 comprises a radially expandable woven mesh or coil basket open on the proximal end and closed at the distal end. The mesh may be made from materials well known and understood by artisans, including polymers, fluoropolymers, nitinol, stainless steel, vectran, or kevlar. Other biocompatible materials that may be woven or coiled are similarly contemplated. Mesh basket 210 connects to microcatheter 230 via tethers 220 and is designed to be compatible such that it is removable in its deployed state without causing dissection or other damage to the vasculature.

Mesh basket 210 comprises a plurality of individual cells, having a uniform size or spacing geometry or a variable size or spacing geometry. According to embodiments where the size or spacing geometry is variable, smaller size or spacing geometry is used to provide a tight mesh for preventing the passage of small pieces of embolus 120 that break away. Larger size or spacing geometry units allow from blood flow 110. In all cases, size or spacing geometry will not allow pieces of embolus 120 that may cause potential complications. In some embodiments, the mesh basket 210 comprises struts having increased thickness adjacent to the proximal end 211 of the mesh basket 210 to provide tensile strength for opening the mesh basket 210', such as described in U.S. Provisional No. 61/015,154, filed on Dec. 19, 2007, the entire content of which has been incorporated by reference above. The mesh basket 210 can comprise a woven retrieval basket having low porosity fine wires in the basket area to support a clot and thicker wires at a proximal end that open the retrieval basket and give tensile strength to the retrieval basket. FIGS. 3A-3D illustrate an offset clot basket 210' having struts at a proximal end 212 that have a larger width than the struts along a main body 214 of the clot basket 210'.

Tethers 220 serve to provide structure for mesh basket 210, while providing large openings whereby blood may freely flow from the proximal to distal end of embolus removal device/basket 200. According to embodiments, tethers 220 are made from the same material as mesh basket 210. Those skilled in the art will readily understand that materials for tethers and mesh may be the same, different, or interchangeable, as needed.

During deployment of embolus capture device/basket 200, mesh basket is stored in microcatheter 230 in an undeployed state. In the undeployed state, microcatheter 230 is advanced distal to embolus 120 and mesh basket 210 is deployed. According to embodiments, both mesh basket 210 and tethers 220 are deployed distal to embolus 120 to prevent tethers 220 from dislodging pieces of embolus 120 prior to full expansion of mesh basket 210, thereby preventing the pieces from advancing distal to the embolus 120 before mesh basket 210 is in place to filter them.

After deployment, according to embodiments, embolus removal system 200 is retracted proximally until embolus is substantially contained within mesh basket 210. Thereafter, mesh basket 210 and microcatheter 230 are removed from the vasculature of the patient. During removal of mesh basket 210 and microcatheter 230, embolus 120 is trapped within mesh basket 210 and withdrawn from vessel 110. In some embodiments, a foreign body is the target of removal. The foreign body can comprise, for example, a microcoil, a medical device, a kidney stone, and/or a gallstone.

According to embodiments, microcatheter 230 length and diameter are suitable for inserting into a human patient and capable of reaching a target embolus in the region above the subclavian and common carotid arteries. For example, according to embodiments, microcatheter 230 is about 150 cm long; microcatheter has a proximal segment (at a control end of microcatheter 230) that is about 115 cm long with an outer diameter of about 3.5 French and a distal segment (at a deployment end of microcatheter 230) is about 35 cm with an outer diameter of about 2.7 French. The inventors contemplate, according to embodiments a gradual decrease or stepwise in the outer diameter dimension as a function of the distal distance from proximal segment, according to embodiments. For example, proximal segment is 3.5 French at the most proximal end and distal segment is 2.7 French at the most distal end. Disposed between is a segment having one or more intermediate outer diameters between 3.5 French and 2.7 French, such as 3.2 French and 3.0 French. The inner diameter of microcatheter 230 is 0.012 to 0.029 inches, according to embodiments, which allows microcatheter to be inserted along a preinserted guidewire or used to infuse therapeutic agents. According to embodiments, the performance of microcatheter 230 is comparable to standard microcatheters 230 and is designed to track over a guidewire through the neurovasculature.

Figure 4:
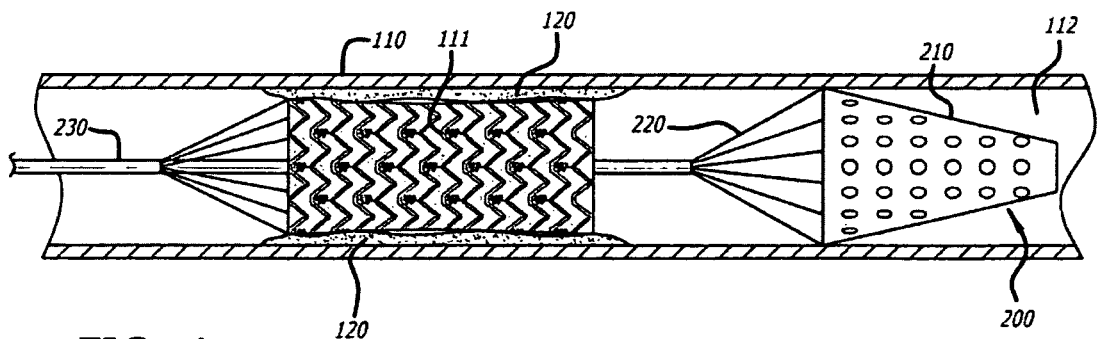
FIG. 4 is a side view of an embodiment of a device for capturing emboli according to the present invention used as a safety device in a reperfusion operation.

As illustrated by embodiments in FIG. 4, embolus capture device/basket 200 may be deployed concurrently with a tethered reperfusion device 111. As embolus 120 is reperfused with reperfusion device 111, embolus capture device/basket 200 provides a safety feature whereby pieces of embolus 120 that break away are captured in mesh basket 210 and removed with the reperfusion device generally. Additionally, as vessel 110 reperfuses due to natural lytic action, mesh basket 210 provides a minimum particle size permitted to pass distal to embolus capture device/basket 200. Consequently, embolus capture device/basket 200 prevents further complications distal to the original site of the occlusion by preventing larger embolus 120 pieces or particles from passing deeper into the neurovasculature and occluding it in more distal locations.

Figure 5:
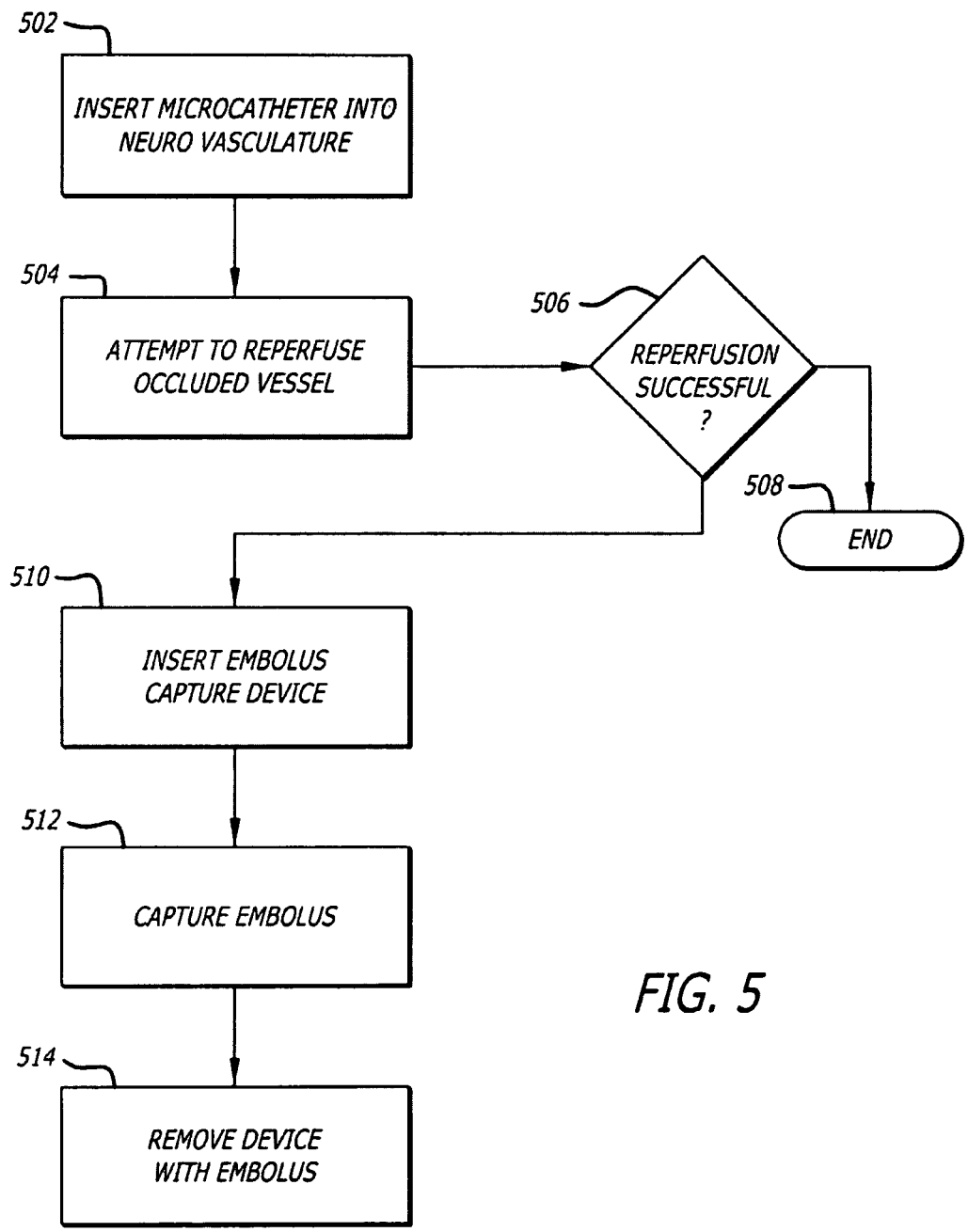
FIG. 5 is a flow diagram of an embodiment of a method wherein an embolus is removed from a patient after a reperfusion operation is unsuccessful.

Alternately and as illustrated according to embodiments in FIG. 5, the embolus capture device/basket 200 is used after reperfusion is unsuccessfully attempted or not successful to the desired level. Accordingly, microcatheter is inserted into the neurovasculature in operation 502 as well known and understood by artisans. Reperfusion is attempted, for example, with the reperfusion device 111 of FIG. 5 in operation 504 of FIG. 5. In some embodiments, a catheter-revascularization system is deployed through a patient's blood vessels. Once the user of catheter-revascularization system determines that the embolus to be addressed is crossed, a revascularization device (e.g., reperfusion device 111) is deployed by first positioning an outer catheter (e.g., microcatheter 230) in a location immediately distal to the embolus. Then, to revascularize, or reperfuse, the occluded blood vessel, the reperfusion device is deployed in a location whereby the reperfusion device expands at the location of the embolus. The embolus is thereby compressed against the luminal wall of the blood vessel and blood flow is restored. After reperfusion is attempted, the success is determined in operation 506. For example, a contrast dye is used to determine the level to which the occluded vessel is reperfused, as is well known to artisans.

Figure 6:
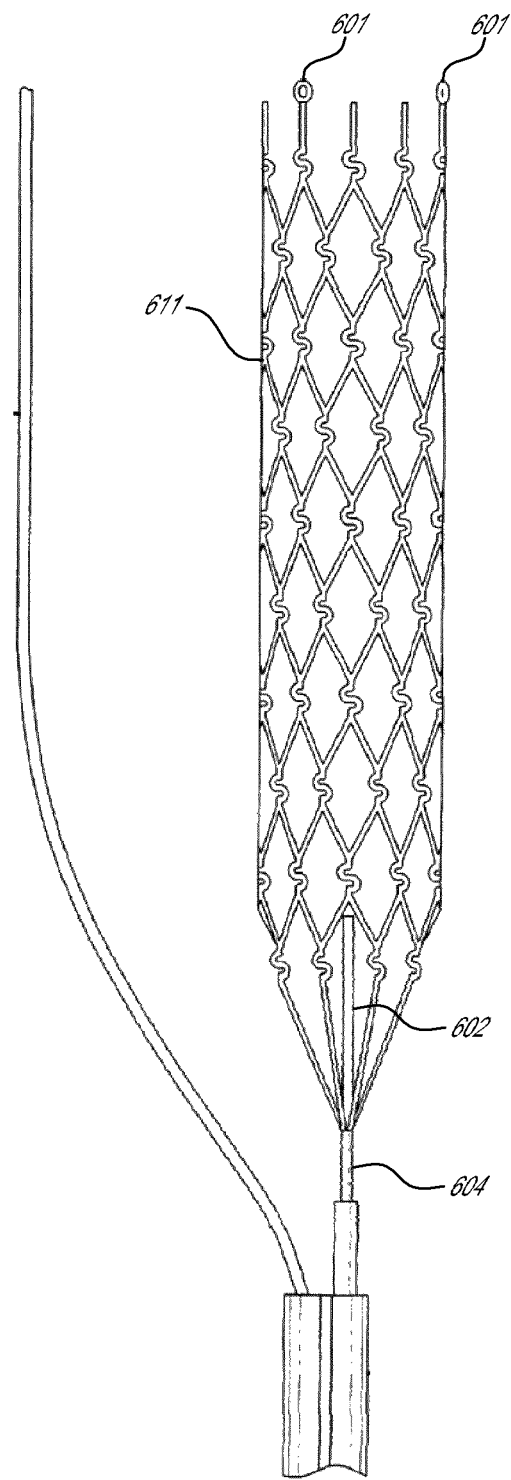
FIG. 6 illustrates an embodiment of a stroke device.

In some embodiments, the embolus capture device/basket 200 has radiopacity at a distal end of the device. The radiopacity may comprise at least a peg, selected from the group consisting of platinum and gold, the peg being pressed into pre-laser cut apertures at a distal end of the mesh basket. FIG. 6 illustrates a device having markers 601 that have been pressed into pre-laser cut apertures at a distal end of the device. In one embodiment, the device comprises a nitinol cut tube and a stainless steel hypotube, as described in U.S. Provisional Application No. 61/015,154, filed on Dec. 19, 2007, the entire content of which has been expressly incorporated by reference above. In some embodiments, the device comprises a stainless steel pusher with a distal nitinol device, as described in U.S. application Ser. No. 12/123,390, filed on May 19, 2008, the contents of which has been expressly incorporated by reference above. With reference to FIG. 6, in one embodiment, a polymeric liner 602 is incorporated within a pusher 604 to improve guidewire trackability. The polymeric liner 602 can be extended beyond the distal tip of the pusher 604. In accordance with some embodiments, guidewire entanglement in the nitinol device 611 is prevented by the extended polymeric liner 602.

If reperfusion is not successful to a desired degree, then embolus capture device/basket 200 is inserted through the microcatheter as described herein and deployed distal to the embolus 120. For example, creating a channel for flow ideally includes making a vessel at least about halfway patent, or 50% of diameter of a vessel being open. According to embodiments, the channel created may be a cerebral equivalent of thrombolysis in myocardial infarction (TIMI) 0, TIMI 1, or TIMI 2, TIMI 3, and thrombolysis in cerebral infarction (TICI) and TICI 3. In these cases, blood flow is not accomplished to a desired degree. It is therefore desirable to remove the entire embolus. Thus, after embolus capture device/basket 200 is deployed distal to the embolus, it is retreated proximal until embolus 120 is substantially inside of mesh basket 210 in operation 512. Thereafter, mesh basket 210, embolus 120, and microcatheter 230 are removed.

The embolus capture devices of the present invention may be designed for over the wire deployment or rapid exchange deployment, according to embodiments.

Expressly incorporated herein by reference as if fully set forth herein are U.S. Pat. Nos. 5,928,260 and 5,972,019 along with U.S. Pat. Nos. 7,147,655; 7,160,317; 7,172,575; 7,175,607; and 7,201,770.

Figure 7A:
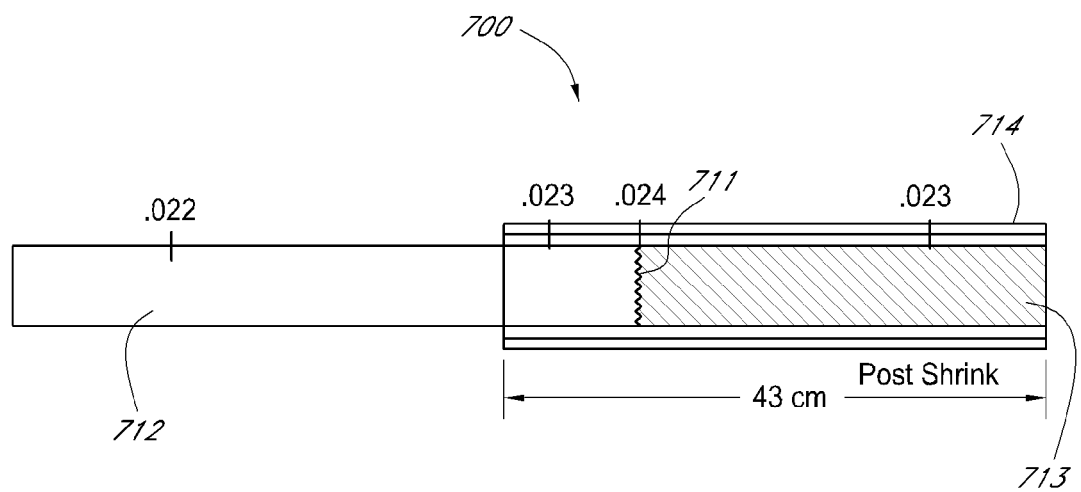
FIGS. 7A and 7B illustrate embodiments of delivery device assemblies.
Figure 7B:
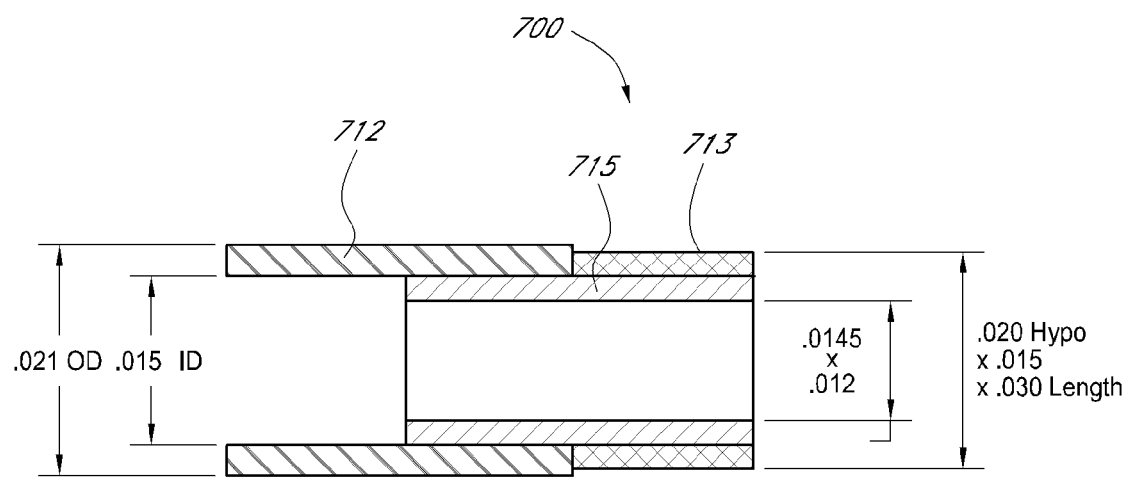

As excerpted from U.S. Provisional Application Ser. No. 61/015,154, filed Dec. 19, 2007, which is expressly incorporated herein by reference, FIGS. 7A and 7B illustrate embodiments of delivery device assemblies.

In one embodiment, ischemic stroke reperfusion or clot capture is performed by a reperfusion device or embolus capture device comprising a NiTi cut tube.

One embodiment for ischemic stroke clot retrieval includes an eccentric design. This embodiment addresses the problem during clot removal of the thrombectomy device being forced off-center because of microcatheter positioning after the microcatheter/guidewire passes the embolus. This "off-centering" causes the device to miss the embolus when pulled proximal to attempt to capture it or fragmenting will occur because the device will shave the embolus. In some embodiments, an off center delivery system is used to capture the embolus. In some embodiments, the struts are designed or favored to the periphery of the artery as opposed to the center of the artery. In some embodiments, the struts are designed to accumulate in 270 degrees of the thrombectomy device allowing open space for the embolus to fall into. By making the attachment point off-center, the open area is increased. By making the device off-center from the point of attachment to the delivery system, the device must increase the chance of capturing the embolus, which is also off-center from the microcatheter.

The chart below illustrates several ischemic stroke delivery system assembly embodiment options:

| 1st Option | | 2nd Option | |
|---|---|---|---|
| Hypo: (24 TW) | .022" × .014" | Hypo: | .0215" × .0155" |
| Ribbon Coil: | .003" × .005" × .015" | Ribbon Coil: | .003" × .005" × .015" |
| PET Heat Shrink: | .027" × .00025" Wall | PET Heat Shrink: | .027" × .00025" Wall |
| or | .028" × .0004" Wall | | |

| 3rd Option | | 4th Option | |
|---|---|---|---|
| Hypo: | .022" × .014" | Hypo: | .0215" × .0155" |
| Ribbon Coil: | .003" × .010" × .015" | Ribbon Coil: | .003" × .010" × .015" |
| PET Heat Shrink: | .027" × .00025" Wall | PET Heat Shrink: | .027" × .0025" Wall |
| or | .028" × .0004" Wall | | |

In some embodiments, the delivery systems maintain an outer diameter at the solder joint of 0.024" max. In some embodiments, the PET heat shrink is installed over the distal 45 cm of the delivery device. In some embodiments, the distal tip of the delivery system is trimmed after installation of the PET heat shrink. In some embodiments, the distal and proximal ends of the delivery system are deburred. In some embodiments, the delivery systems must accept a 0.010" guidewire.

FIG. 7A illustrates embodiments of a distal end of a hypotube assembly 700 that includes a solder joint 711 between a hypotube 712 and a ribbon coil 713 and a PET heat shrink 714. FIG. 7A illustrates example outer diameter and length dimensions of the delivery system assembly.

The chart below illustrates dimensions for embodiments of the hypotube assembly, or delivery system.

| Design | Hypotube OD | Ribbon Coil | PET | PET Prox | PET @ Joint | PET Distal |
|---|---|---|---|---|---|---|
| 1 | .022" × .014" 24 TW | .003" × .005" × .015" | 0.027" × .00025" × 45 cm | .023" | .024" | .023" |
| 2 | .022" × .014" 24 TW | .003" × .010" × .015" | 0.027" × .0025" × 45 cm | .023" | .024" | .023" |
| 3 | .0215" × .0155" | .003" × .005" × .015" | 0.027" × .0004" × 45 cm | .022" | .025" | .0225"/ .023" |
| 4 | .0215" × .0155" | .003" × .010" × .015" | 0.027" × .0004" × 45 cm | .022" | .025" | .0225"/ .023" |
| 5 | .022" × .014" | .002" × .010" × .017" | 0.028" × .0004" × 45 cm | .022" | .0245" | .023"/ .025" |

The embodiments disclosed in the tables above accept a 0.010 G.W. (guidewire) straight. In some embodiments, the distal tip of the hypotube 712 is ground (e.g., to 0.0175") to accept the inner diameter (e.g., 0.015") of the ribbon coil 713. The distal tip of the hypotube 712 is soldered to the proximate tip of the ribbon coil 713. The PET 714 is cut to 45 cm, the heat shrink is heated to 400 degrees Fahrenheit, and restrained while heated.

Example 1

In Vitro Tracking Evaluation Test

A study was performed to evaluate in-vitro tracking of embodiments of delivery system. The testing equipment included: a FlowTek A201 with stroke model, a 5F CORDIS® ENVOY™ MPD guide catheter, a 135 cm×0.027" inner diameter CORDIS® MASS TRANSIT™ microcatheter, and a 0.010 diameter×200 cm length TRANSEND® guidewire. The study used the following numbered scoring system: (1) pass with no friction at all; (2) pass with acceptable friction; (3) pass with some friction; (4) pass with difficulty; (5) can't pass.

| Design # | Curve 1 | Curve 2 | Curve 3 | Curve 4 | PCOM | A1/M1 | M2/M3 |
|---|---|---|---|---|---|---|---|
| 1 | 2/3 | 2/3 | 2/3 | 2/3 | 2/3 | 2/3 | 2 |
| 2 | 3 | 3 | 3 | 3 | 3 | 3 | 2 |
| 3 | N/A | N/A | N/A | N/A | N/A | N/A | N/A |
| 4 | 2 | 2 | 2 | 2 | 2 | 2 | 2 |
| 5 | 1 | 1/2 | 1/2 | 1/2 | 1/2 | 1/2 | 1/2 |

The following notes were taken from the study regarding guidewire tracking. Design 1 passed fine until the PCOM segment with a score of 4. Design 2 experienced some friction requiring 300 cm of exchange wire with a score of ¾. Design 4 scored a 5 at curve 4. Design 5 scored a 4 generally. Designs 3 and 4 had a 0.0155" inner diameter and designs 1 and 2 had a 0.014" inner diameter. Design 5 had a 0.002"×0.010"× 0.018" hypotube ribbon coil.

FIG. 7B illustrates an embodiment of a distal end of a delivery system assembly 700. In one embodiment, the delivery system assembly 700 includes a proximal hypotube 712, a distal braid 713 and a polyimide liner 715. In one embodiment, the polyimide liner 715 may be a braid. In one embodiment, the braid needs 0.00065" wire.

Strut thicknesses for the recanalization or reperfusion devices described herein can include 0.0040", 0.0025", 0.0020", and 0.0009". The strut thicknesses may vary. The devices may be used for reperfusion and may be tethered. The devices may or may not be recapturable and may or may not include markers.

In some embodiments, the devices described herein are be used for clot removal and comprise a clot basket or spiral basket. In one embodiment, the clot removal device comprises a woven retrieval basket. The woven retrieval basket may include features such as an over the wire design, low porosity fine wires in the basket area to support a clot (wire dia: 0.035 mm and 56-97 pics/cm), or thicker wires that open the basket and give it tensile strength (wire dia: 0.076 mm). The woven retrieval basket may also be fully automatable.

In another embodiment, a reperfusion catheter device includes a nitinol braid. In one embodiment, the braid includes 24 strands with a wire size of 0.076 mm, a braid angle of 42 degrees, an expanded diameter of 3.5 mm, and a collapsed diameter of approximately 0.030". Other disclosure can be found in U.S. Provisional No. 61/015,154, which is expressly incorporated herein by reference.

As excerpted from U.S. Provisional No. 61/057,613 filed May 30, 2008, which is expressly incorporated herein by reference, devices and methods for restoring blood flow and embolus removal during acute ischemic stroke are provided.

In accordance with several embodiments, many of the positives of stenting can be combined with revascularization/reperfusion using devices effective to impact and remove embolus. This trend now applies in the brain, and promises dramatic improvements in therapies and treatments.

The pathological course of a blood vessel that is blocked is a gradual progression from reversible ischemia to irreversible infarction (cell death). A stroke is often referred to as a "brain attack" and occurs when a blood vessel in the brain becomes blocked or ruptures. An ischemic stroke occurs when a blood vessel in the brain becomes blocked. Ischemic strokes comprise about 78% of all strokes. A hemorrhagic stroke, which account for the remaining 22% of strokes, occurs when a blood vessel in the brain ruptures. Stroke is the third leading cause of death in the United States, behind heart disease and cancer and is the leading cause of severe, long-term disability. Each year roughly 700,000 Americans experience a new or recurrent stroke. Stroke is the number one cause of inpatient Medicare reimbursement for long-term adult care. Total stroke costs now exceed $45 billion per year in US healthcare dollars.

Viable tissue that surrounds a central core of infarction has consistently been demonstrated in animal models to be salvageable if blood flow can be restored within a time window of several hours. Data from human studies with surrogate measurements of cell viability tended to support this hypothesis. Thus, current treatment strategy for ischemic stroke is based on an urgent restoration of blood flow to the ischemic tissue within the tolerance time window to prevent the permanent loss of brain cells, leading to improved outcome for the patient.

According to the instant disclosure, if autolysis is not occurring then capture of the embolus/blood clot in its entirety without fragmenting the embolus and removal of the embolus/blood clot from the body without creating a new stroke in a new territory is performed.

According to some embodiments, the system will allow maintained arterial access to the treatment site and provide greater support to the arterial tree by being either over-the-wire (OTW) or rapid exchange (RX). This feature will enable the embolus/blood clot to be securely captured and removed by providing support within the vessel. The OTW or RX support provided will prevent the proximal vessel from buckling or kinking during tensioning upon embolus removal. Buckling or kinking of the vessel causes the proximal vessel orifice to ovalize, thereby stripping the embolus from the capture device.

In some embodiments, emboli can be removed while reperfusion is taking place using a variety of devices in the neural space.

Using everted basket-like members and everted stent-like members, emboli can be removed without compromising access, as they become enmeshed with the devices and can be removed without vessel damage.

In one embodiment, an occluded artery, for example, at the MCA/ACA bifurcation is accessed with a microcatheter, then a clot is accessed using the subject reperfusion/clot removal device, allowing for reperfusion by the reperfusion/clot removal device.

In one embodiment, the reperfusion/clot removal device engages the clot by impacting the same. The nature of the open-cell structure of the device grabs the clot, which is then slowly pulled back until it can be drawn into the carotid siphon and then removed into the cavernous carotid, then the common carotid and eventually removed from the body.

Figure 8:
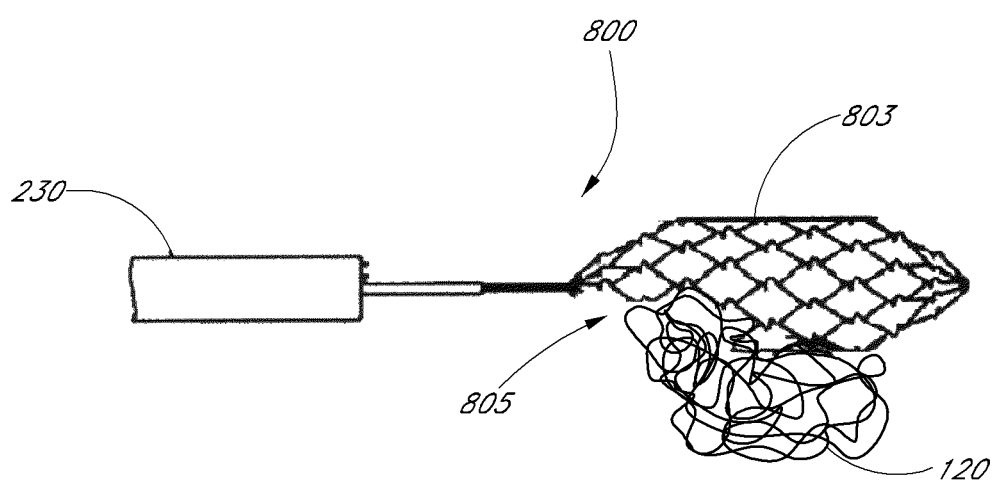
FIG. 8 illustrates an embolus caught in an external distal tip of an embodiment of a reperfusion/clot removal device.
Figure 10A:
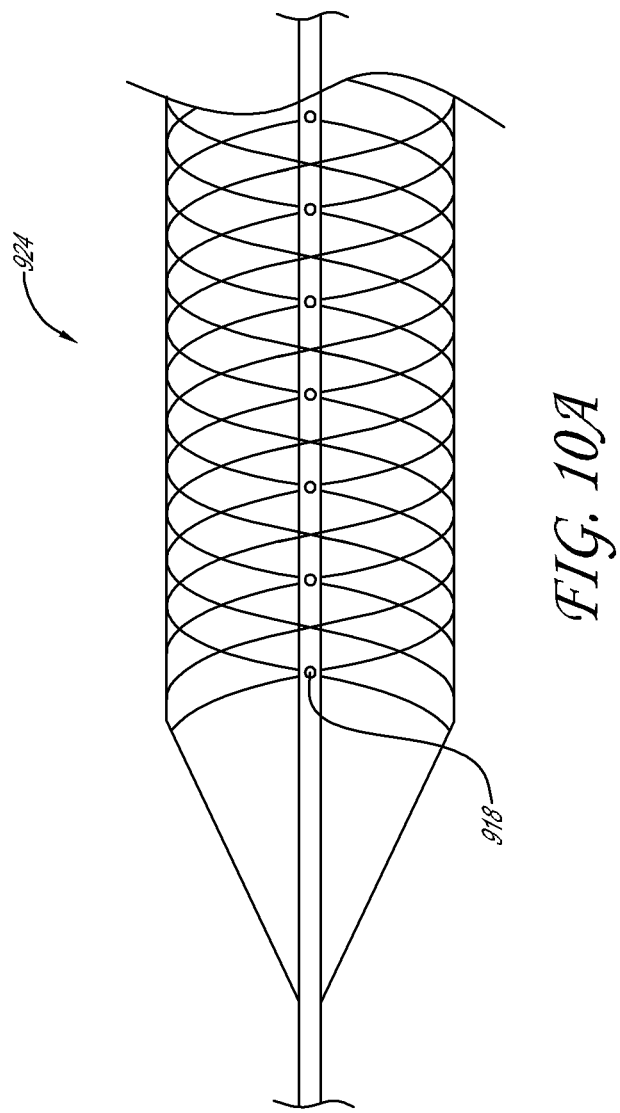
FIG. 10A illustrates a detailed view of the inner catheter of FIG. 10.
Figure 12A:
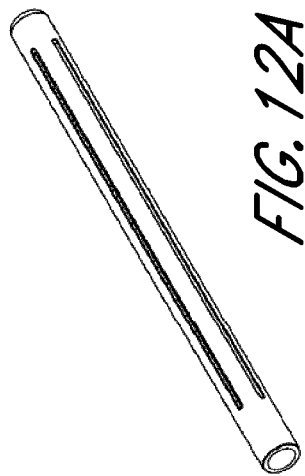
Figure 12B:
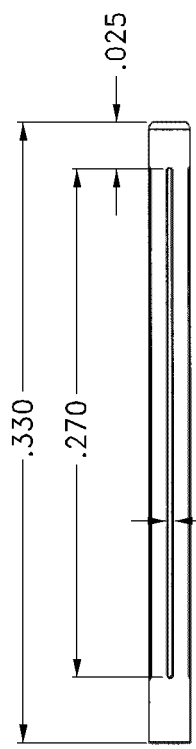
Figure 12C:
Figure 13A:
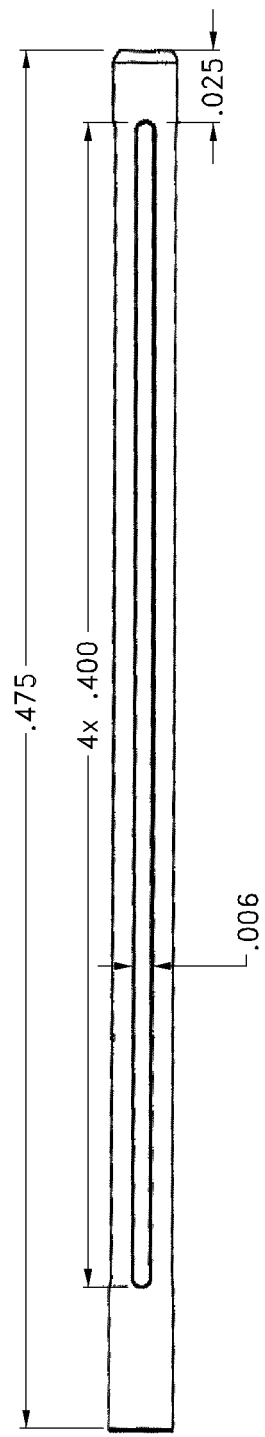
Figure 14A:
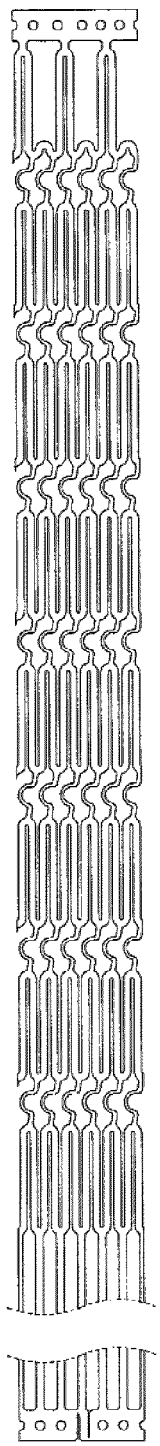
Figure 14D:
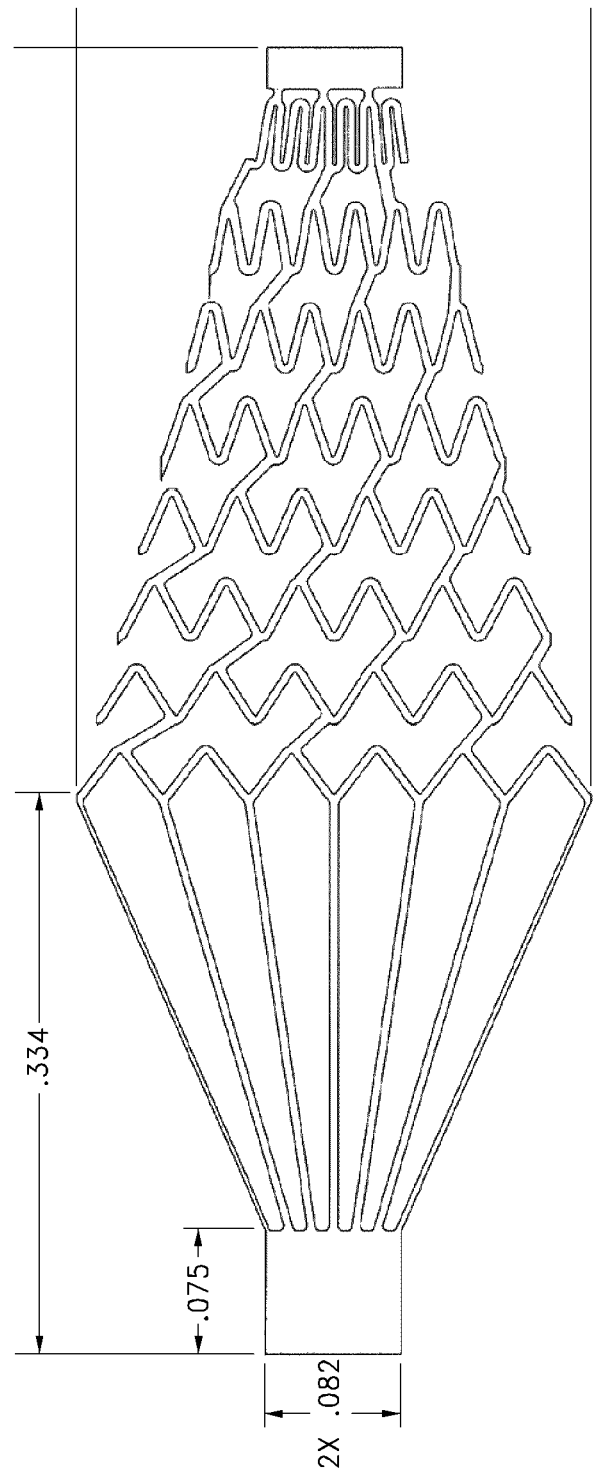
Figure 15A:
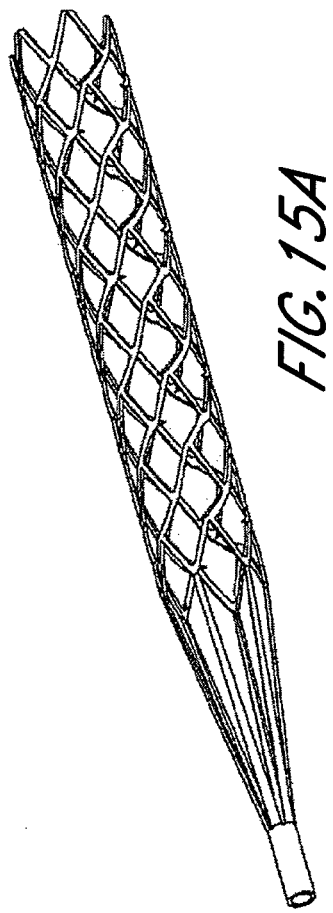
Figure 15B:
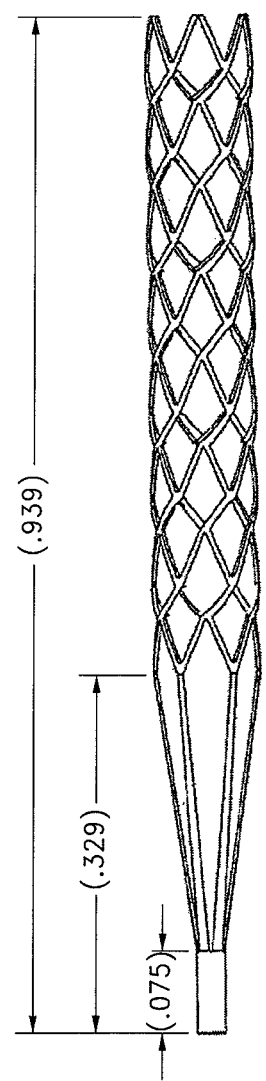
Figure 15D:
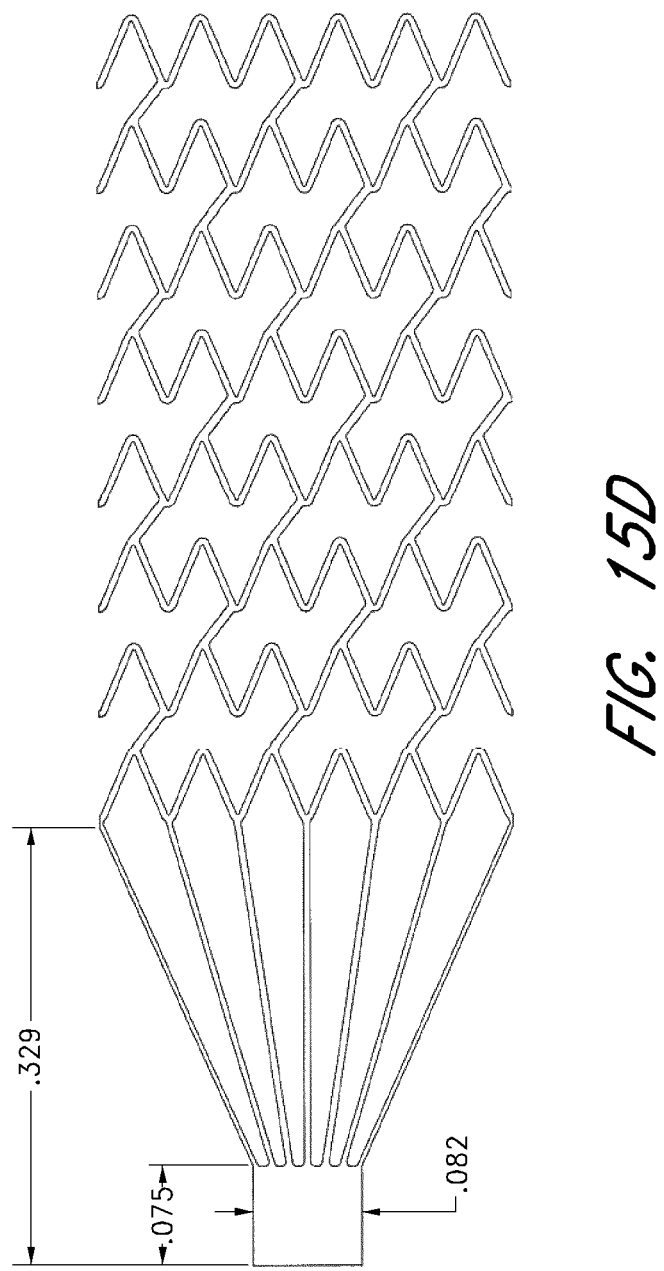
Figure 16A:
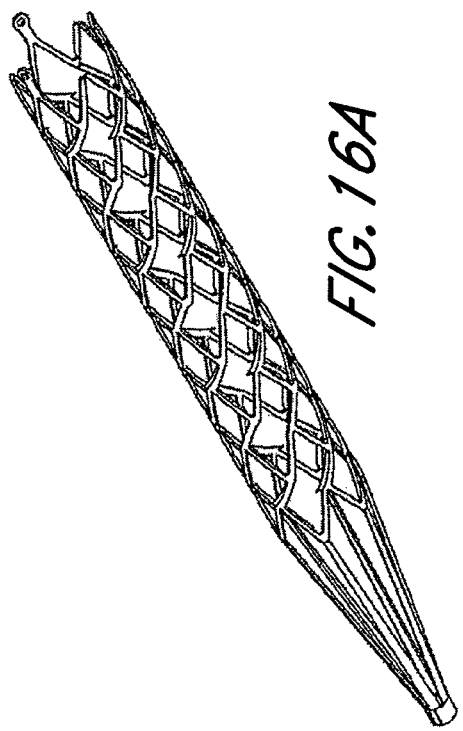
Figure 16B:
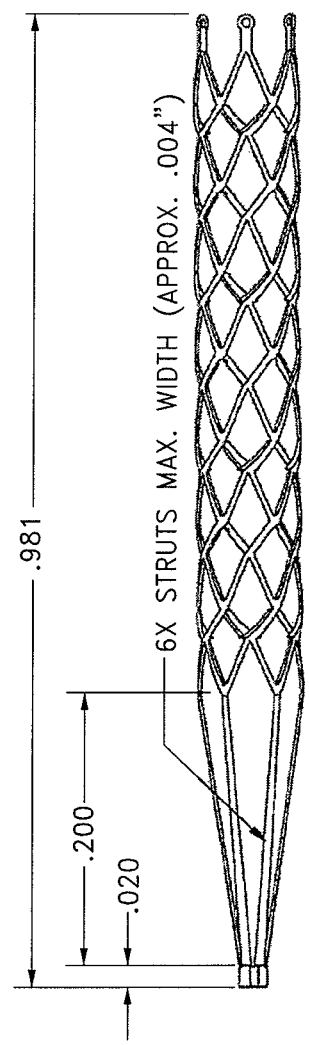
Figure 16C:
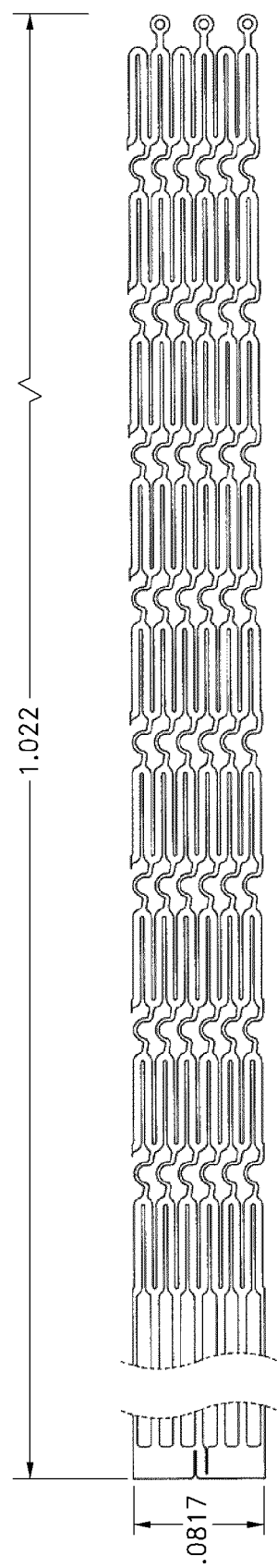
Figure 17A:
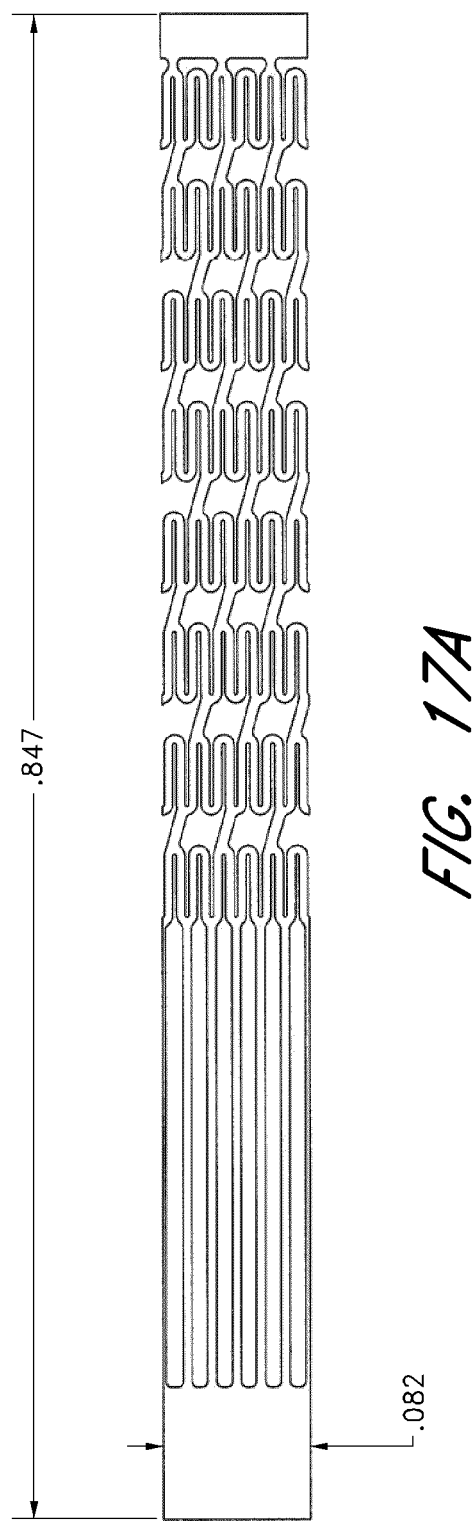
Figure 17B:
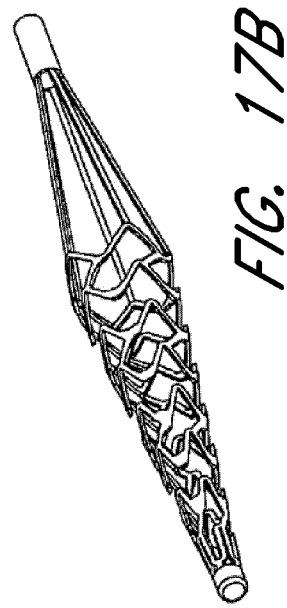
Figure 17C:
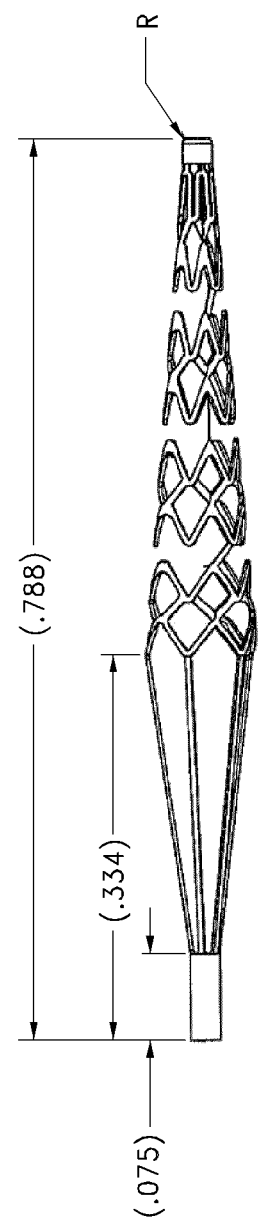
Figure 18:
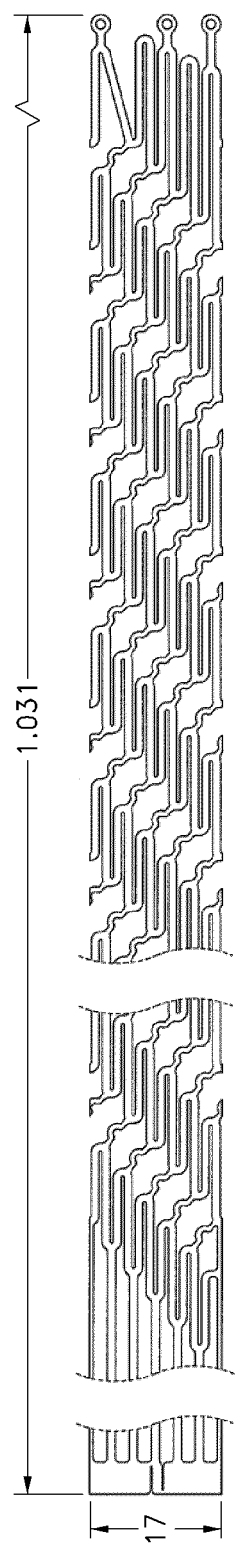
Figure 19:
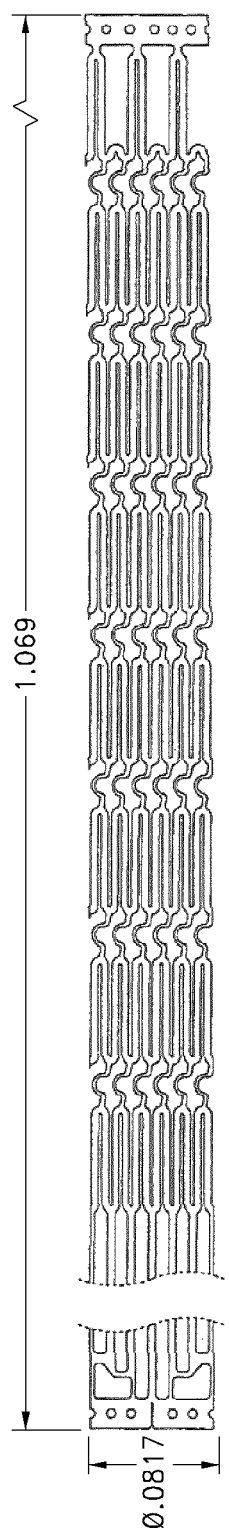
Figure 20D:
Figure 20E:
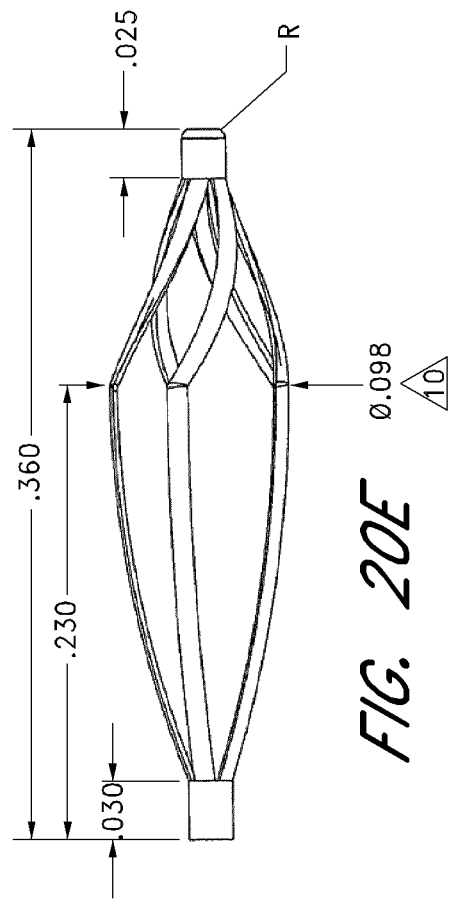
Figure 20F:
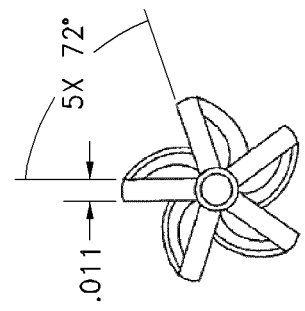

Those skilled in the art readily understand how this procedure applies to other neuro-vessels. FIG. 8 illustrates an embolus 120 caught in an external distal tip of an embodiment of a reperfusion/clot removal device 800. The reperfusion/clot removal device has an open "mouth" 805. The mouth 805 spans from a proximal tip of the device 800 to approximately a mid-section of the device 800. The clot, or embolus, appears to be partially caught in the mouth 805 of the reperfusion/clot removal device 800 but partially on the external surface of the distal basket region 803 of the device 800. In one embodiment, the size of the clot, or embolus, is decreased from 4-5 mm in diameter and 15 mm in length to 4 mm in diameter and 10 mm in length.

Example 2

Clotting Characteristics of Swine Blood for Testing Purposes

A study was performed to evaluate swine blood for clotting characteristics under certain handling conditions. The materials used in the test included: (1) 1 liter of pig blood (no anti-coagulant), (2) Pyrex® glassware, (3) Clorox® bleach, (4) syringes, and (5) saline consisting of a multi-purpose no rub isotonic solution, (In accordance with one embodiment, the testing procedure was performed as follows: (1) pour pig blood into glassware, (2) allow pig blood to sit for 90 minutes, (3) wash the pig blood with saline, (4) allow to sit for 60 minutes, (5) remove "white" clot with cutting tools, (6) wash thoroughly with saline, and (7) measure clot dimensions. The dimensions of the clot removed from the pig blood had a length of 50 mm and a diameter ranging from 7 to 10 mm. Other disclosure can be found in U.S. Provisional No. 61/057,613, which is expressly incorporated herein by reference.

As excerpted from U.S. application Ser. No. 12/123,390, filed Apr. 19, 2008 and from U.S. Provisional No. 60/980,736, filed Oct. 17, 2007, which are expressly incorporated herein by reference, FIGS. 9, 10, 10A, 11A-11D, 12A-12F, 13A-13C, 14A-14D, 15A-15D, 16A-16C, 17A-17C, 18, 19, and 20A-20F illustrate various embodiments of revascularization and/or embolus removal devices. In various embodiments, the revascularization and/or embolus removal devices comprise an open distal end and a generally cylindrical body (see, for example, FIGS. 15A-15D and 16A-16C).

According to embodiments and as illustrated in FIG. 9, catheter-based revascularization system 900 provides a platform for lysing emboli in occluded blood vessels. Accordingly, catheter-based revascularization system 900 generally comprises control end 902 and deployment end 904. According to embodiments, control end 902 is a portion of the device that allows a user, such as a surgeon, to control deployment of the device through the blood vessels of a patient. Included as part of control end 902 is delivery handle 906 and winged apparatus 908, in some embodiments. Those skilled in the art readily understand module 913 (see FIG. 10) is detachable.

According to some examples of the instant system during shipping of catheter-revascularization system 900, shipping lock (not shown) is installed between delivery handle 906 and winged apparatus 908 to prevent deployment and premature extension of revascularization device 924 (see FIG. 10) while not in use. Furthermore, by preventing delivery handle 906 from being advanced towards winged apparatus 908, coatings applied to revascularization device 924 are stored in a configuration whereby they will not rub off or be otherwise damaged while catheter-based revascularization system 900 is not in use.

According to embodiments, agent delivery device 930 provides a conduit in fluid communication with the lumen of the catheter-based revascularization system 900 enabling users of the system to deliver agents through catheter-revascularization system 900 directly to the location of the embolus. The instant revascularization system delivery device may be made from materials known to artisans, including stainless steel hypotube, stainless steel coil, polymer jackets, and/or radiopaque jackets. In one embodiment, the revascularization systems comprise a plurality of apertures 918 allowing infusable lytic agents to exit radially and distally into at least a subject embolus when transmitted through agent delivery device which is in fluid communication therewith. The revascularization systems according to several embodiments herein can comprise radiopacity for imaging purposes.

Accordingly, luer connector 932 or a functional equivalent provides sterile access to the lumen of catheter-based revascularization system 900 to effect delivery of a chosen agent. Artisans will understand that revascularization devices of the present invention include embodiments made essentially of nitinol or spring tempered stainless steel. Revascularization devices likewise may be coated or covered with therapeutic substances in pharmacologically effective amounts or lubricious materials. According to embodiments, coatings include nimodipine, vasodialators, sirolamus, and paclitaxel. Additionally, at least heparin and other coating materials of pharmaceutical nature may be used.

Deployment end 904 of catheter-based revascularization system 900 comprises proximal segment 910 and distal segment 920. Proximal segment 910, according to embodiments, houses distal segment 920 and comprises outer catheter 912 that is of a suitable length and diameter for deployment into the blood vessel of the neck, head, and cerebral vasculature. For example in some embodiments, proximal segment 910 is from at least about 100 cm to approximately 115 cm long with an outer diameter of at least about 2.5 French to about 4 French.

Referring also to FIG. 10, distal segment 920 comprises inner catheter 922 and revascularization device 924 (as shown here in one embodiment having uniform cells, variable cells likewise being within other embodiments of the present invention), which is connected to inner catheter 922. Inner catheter 922, according to embodiments, is made from stainless steel coil, stainless steel wire, or ribbon or laser cut hypotube and is of a suitable length and diameter to move through outer catheter 912 during deployment. For example, inner catheter 922 extends from outer catheter 912 38 cm, thereby giving it a total length of between at least about 143 and 175 cm (or between about 143 and 150 cm). The diameter of inner catheter 922 according to the exemplary embodiment is 2.7 French, with an inner diameter of at least about 0.012 to 0.029 inches (or at least about 0.012 to 0.021 inches). The inner diameter of inner catheter 922 may be any suitable diameter provided inner catheter 922 maintains the strength and flexibility to both deploy and retract revascularization device 924. In one embodiment, an inner catheter 922' comprises a variable-pitch hypotube, as shown in FIGS. 11A-D. In some embodiments, the hypotube has an outer diameter of 0.025", 0.022", or 0.016" and an inner diameter of 0.017" or 0.008". In some embodiments, the hypotube comprises a 25TW hypotube or a 31TW hypotube. In one embodiment, the inner catheter 922' comprises a laser-cut, variable-pitch hypotube. Region L comprises a laser cut transition region of the variable-pitch hypotube. Regions P1, P2 and P3 comprise three regions of the variable-pitch hypotube having variable pitch. In one embodiment, the pitch decreases from region P1 to region P2 and from region P2 to region P3.

Referring to FIGS. 9 and 10, revascularization device 924 is a self-expanding, reconstrictable retractable device tethered to inner catheter 922. Revascularization device 924 may be made from nitinol, spring tempered stainless steel, or equivalents as known and understood by artisans, according to embodiments. Revascularization device 924, according to embodiments and depending on the particular problem being addressed, may be from at least about 3.5 mm to about 50 mm in its expanded state. In an expanded state, revascularization device 924 is designed to expand in diameter to the luminal wall of blood vessel where it is deployed.

As known to artisans, revascularization device 924 may be coated or covered with substances imparting lubricous characteristics or therapeutic substances, as desired. Naturally, the expandable mesh design of revascularization device 924 must be a pattern whereby when revascularization device 924 is retracted, it is able to fully retract into inner catheter 922. The nature of the cell type likewise changes with respect to the embodiment used, and is often determined based upon nature of the clot.

Catheter-revascularization system 900 is deployed through a patient's blood vessels. Once the user of catheter-revascularization system 900 determines that the embolus to be addressed is crossed, as known and understood well by artisans, revascularization device 924 is deployed by first positioning outer catheter 912 in a location immediately distal to the embolus.

Then, to revascularize/reperfuse the occluded blood vessel, distal catheter 920 is deployed in a location whereby revascularization device 924 expands at the location of the embolus, as illustrated by FIG. 10. The embolus is thereby compressed against the luminal wall of the blood vessel and blood flow is restored. Modular detachable segment 913 is known also, and may be swapped out, as needed, if an Rx system is used.

As discussed above and claimed below, creating a channel for flow ideally includes making a vessel at least about halfway-patent, or 50% of diameter of a vessel being open. According to other embodiments, the channel created may be a cerebral equivalent of thrombolysis in myocardial infarction TIMI 1, TIMI 2, or TIMI 3.

Restoration of blood flow may act as a natural lytic agent and many emboli may begin to dissolve. Revascularization device 924 is designed, according to embodiments, to radially filter larger pieces of the dissolving embolus and prevent them from traveling distal to the device and potentially causing occlusion in another location. Because the revascularization device provides continuous radial pressure at the location of the obstruction, as the embolus dissolves, the blood flow continues to increase.

After the embolus is lysed, revascularization device 924 is sheathed into outer catheter 912 and removed from the body. According to embodiments, larger pieces of the thrombus may be retracted with revascularization device 924 after being captured in the radial filtering process. According to embodiments, revascularization device 924 may be detachable whereby the revascularization device 924 may detach from catheter-based revascularization system 900 if it is determined that revascularization device 924 should remain in the patient. As discussed above and as illustrated in FIGS. 9 and 10, according to embodiments, catheter-based revascularization system 900 reconstrainable attachment or attachment by tether may be optionally detachable. Revascularization device detachment methods comprise mechanical, electrical hydraulic, chemical, thermal, and those other uses known to artisans. Other disclosure can be found in U.S. application Ser. No. 12/123,390, which is expressly incorporated herein by reference.

As excerpted from U.S. Provisional No. 60/987,384, filed Nov. 12, 2007, which is expressly incorporated herein by reference, FIGS. 21A, 21B, 22A, 22B, 23A, 23B, 24A, 24B, 25A, 25B, 26A-26E, 27A-27D illustrate various embodiments of rapid reperfusion devices. In one embodiment, a microcatheter having an active segment reperfuses occluded blood vessels above the junction of the subclavian artery and common carotid artery. The microcatheter is used to penetrate emboli. Once an embolus is penetrated, the active segment of the microcatheter is activated, causing it to expand radially and thereby open a channel for restored blood flow in the embolus. The blood's natural lytic action further degrades the embolus in some cases. Therapeutic agents may be administered through the microcatheter to aid in the reperfusion process. Active and passive perfusion are thus both enabled. In one embodiment, a device is disclosed comprising a distal segment having attached thereto a radially expandable active segment, a proximal segment comprising an active segment activator for radially expanding or retracting the active segment, an activation member connecting the active segment activator to the active segment. The distal segment is of a suitable diameter for use above the juncture of the subclavian artery and common carotid artery.

In one embodiment, a method is disclosed comprising providing a microcatheter having at least a distal segment, proximal segment, and active segment for use above the subclavian artery and common carotid artery, wherein the active segment is radially expandable.

In one embodiment, a catheter system for use above the juncture of the subclavian artery and common carotid artery is provided, although other uses are equally appropriate as determined by qualified medical personnel and may be introduced via a guidewire. The device operates as a standard microcatheter during introduction into a patient. The distal segment, which is remotely deployable, has attached to it an active segment that expands radially to reperfuse emboli. After reperfusion, the active segment is returned to its configuration prior to expansion and the entire microcatheter system is removed.

According to embodiments and as illustrated by an exemplary embodiment in FIG. 21A, there is shown microcatheter 1100. Microcatheter 1100 comprises proximal segment 1102 and distal segment 1104. Proximal segment 1102 remains outside of the patient and is used to insert and retract microcatheter 1100, as well as deploy active segment 1110 of distal segment 1104 during operation.

According to embodiments, catheter length and diameter are suitable for inserting into a human patient and capable of reaching a target embolus in the region above the subclavian and common carotid arteries. For example, according to embodiments, microcatheter 1100 is about 150 cm long; proximal segment 1102 is about 115 cm with an outer diameter of about 4 French and distal segment 1104 is about 35 cm with an outer diameter of about 2.7 French. In one embodiment, the microcatheter 1100 is 135 cm long, proximal segment 1102 is 90 cm long, and distal segment 1104 is 45 cm long. In one embodiment, the microcatheter 1100 has an inner diameter of 0.012". The inventors contemplate, according to embodiments a gradual decrease or stepwise in the outer diameter dimension as a function of the distal distance from proximal segment 1102, according to embodiments. For example, proximal segment 1102 is 4 French at the most proximal end and distal segment 1104 is 2.7 French at the most distal end. Disposed between is a segment having one or more intermediate outer diameters between 4 French and 2.7 French, such as 3.4 French and 3.0 French (see FIG. 26A). The inner diameter of microcatheter 1100 is 0.012 to 0.021 inches, according to embodiments, which allows microcatheter to be inserted along a preinserted guidewire or used to infuse therapeutic agents. According to embodiments, the performance of microcatheter is comparable to standard microcatheters and is designed to track over a guidewire through the neuro-vasculature.

According to embodiments, microcatheter 1100 is designed to follow a path of least resistance through a thrombus. Guidewire inserted through a thrombus tends to follow the path of least resistance through the softest parts of each thrombus. When microcatheter 1100 is inserted, it likewise follows this path of least resistance. As blood flow is restored, the natural lytic action further helps to break up the thrombus.

According to embodiments, active segment 1110 comprises a radially expandable woven mesh or coil. The mesh may be made from materials well known and understood by artisans, including polymers, fluoropolymers, nitinol, stainless steel, vectran, or kevlar. Other biocompatible materials that may be woven or coiled are similarly contemplated. Active segment 1110 is, according to embodiments, 5 mm to 50 mm in length when expanded and is designed to substantially return to its preexpansion configuration for removal of microcatheter after reperfusion. In one embodiment, active segment 1110 is 15 mm long.

As indicated above, active segment 1110 comprises a mesh. The mesh comprises a plurality of individual units, having a uniform size or spacing geometry or a variable size or spacing geometry. According to embodiments where the size or spacing geometry is variable, smaller size or spacing geometry is used to provide a tight mesh for expanding a channel through the thrombus. Larger size or spacing geometry units allow from blood flow through active segment 1110. In one embodiment, active segment 1110 comprises a woven polymer mesh that is heparin coated. In one embodiment, active segment 1110 has a suitable porosity to permit blood flow when expanded. In one embodiment, releasing expansion of active segment 1110 will trap thrombus in the mesh.

According to embodiments, variable cell size or spacing geometry is accomplished with points where the braid crosses over fixed filaments (PICS). Thus, the cell size or spacing geometry varies by varying the density of the braid. Where high radial force is needed to open a channel in an embolus, for example, the filaments of the mesh are denser and therefore cross each other more often, yielding small cell size or spacing geometry that leads to the application of greater radial force when the mesh expands. Where perfusion is desired, the PICS are less dense and the resulting cell size or spacing geometry is increased. Additionally, drug delivery through microcatheter will be more effective in mesh configurations having a large size or spacing geometry.

Active segment 1110 may be coated or covered with substances, such as lubricious agents or pharmacologically active agents, according to embodiments. For example, active segment 1110 may be covered with heparin or other agents that are used in clot therapy, such as those that aid in dissolving clots or mitigating vasospasms.

According to similar embodiments, therapeutic agents are deployable through the lumen of microcatheter 1100, thereby allowing users of microcatheter 1100 to determine on a case-by-case basis whether to administer an agent. Accordingly, the braid/geometry of active segment 1110 is porous to allow the agent to pass from lumen of microcatheter 1100 into the blood vessel at the site of an embolus, for example.

Activation member 1120, according to embodiments, is a wire that connects proximal segment 1102 to distal segment 1104 and allows a user of microcatheter 1100 to deploy active segment 1110. Accordingly, activation member 1120 is made from stainless steel wire or braid, composites polymers and metal braids, ribbon or wire coils. According to embodiments, activation member 1120 comprises a hollow lumen that slidably moves over a guidewire to insert microcatheter 1100.

When active segment 1110 is expanded in a vessel, the radial expansion causes a channel to be formed in a thrombus for restored blood flow past the occlusion and thereby reperfuse the vessel. Activation of active segment 1110 is accomplished by mechanical methods, such as with activation member 1120 or by using liner of microcatheter 1110. Use of the liner is accomplished by leaving the liner unfused with active segment 1110.

For example, activation member 1120 fuses to the distalmost portion of activation segment 1110. According to embodiments, activation segment 1110 is heat set into a native confirmation in an expanded state. When activation member 1120 tensions active segment 1110, its confirmation changes from an expanded state into a deliverable state. Once delivered to the site of an embolus, activation member 1120 is adjusted to allow active segment 1110 to relax and thereby expand. According to similar embodiments, active segment 1110 is heat set into a native unexpanded confirmation. Activation member 1120 is used to tension active segment 1110 when delivered to the site of an embolus, thereby expanding it.

Other activation methods include electrical, chemical, and thermal activators, as is known and understood by artisans. Hydraulic activation may be accomplished with a balloon in the interior of the catheter that is filled with a fluid, thereby expanding the balloon, which expands active segment.

According to embodiments illustrated in FIG. 22A, microcatheter is inserted into a vessel having an occlusion. As previously discussed, microcatheter is insertable along a guidewire through vessel lumen 1202, according to certain embodiments. Microcatheter 1100 penetrates embolus 1210 in vessel 1200. Active segment 1110 is positioned to coincide with the position of embolus 1210, according to techniques well known and understood by artisans. Thereafter, active segment 1110 is expanded, thereby opening a channel in thrombus 1210 and restoring blood flow, as illustrated in FIG. 22B.

Once activated, active segment 1110 allows blood to flow around microcatheter 1100 and active segment 1110 to create therapeutic benefits associated with reperfusion. For example and according to embodiments, the portions of distal segment 1104 immediately proximal and distal to active segment 1110 may have a diameter of 2.0 French to 3.0 French and have installed therein revascularization ports 1112, as shown in FIGS. 22A and 22B. Revascularization ports 1112 comprise openings in microcatheter 1100 that allow to blood flow through microcatheter 1100. Additionally, revascularization ports 1112 provide additional delivery points for therapeutic agents delivered through microcatheter 1100.

According to embodiments, a filter may be placed distal of active segment to prevent embolus pieces detached in the reperfusion process from escaping and causing distal occlusions. Accordingly, active segment is designed to capture pieces of embolus during the reperfusion processes. These pieces are captured within active segment 1110 when active segment 1110 is returned to its initial confirmation after expansion.

Figure 23A:
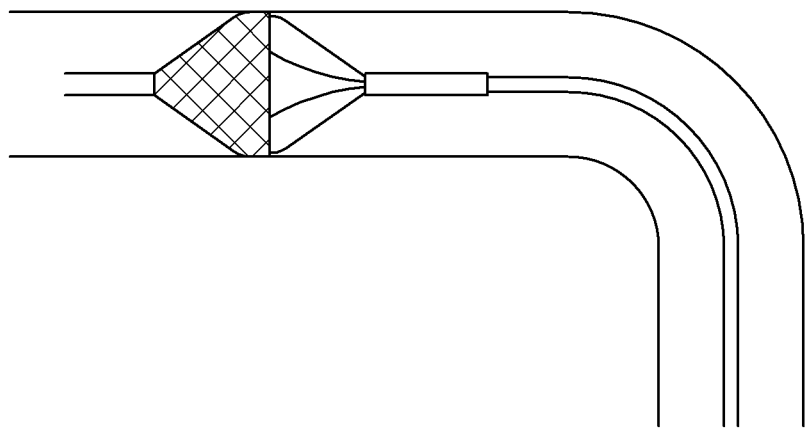
FIG. 23A is a side view of an embodiment of a rapid reperfusion device comprising an infusable microwire with an integrated filter.
Figure 23B:
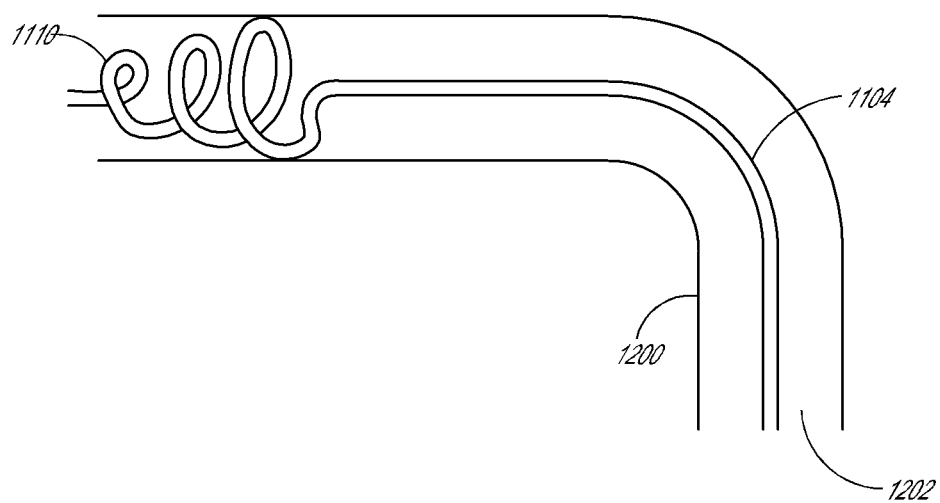
FIG. 23B is a side view of an embodiment of a rapid reperfusion device comprising an infusable coil.

In some embodiments, active segment 1110 comprises an infusable microwire with an integrated filter as illustrated in FIG. 23A. In one embodiment, the infusable microwire has a diameter of 0.014". According to embodiments and as illustrated in FIG. 23B, active segment 1110 comprises an infusable coil. In one embodiment, the infusable coil has a diameter of 0.014". Accordingly, active segment 1110 comprises a large portion of distal segment 1104, wherein microcatheter 1100 itself coils when activated to create a channel through an embolus whereby blood flow is restored.

Figure 24A:
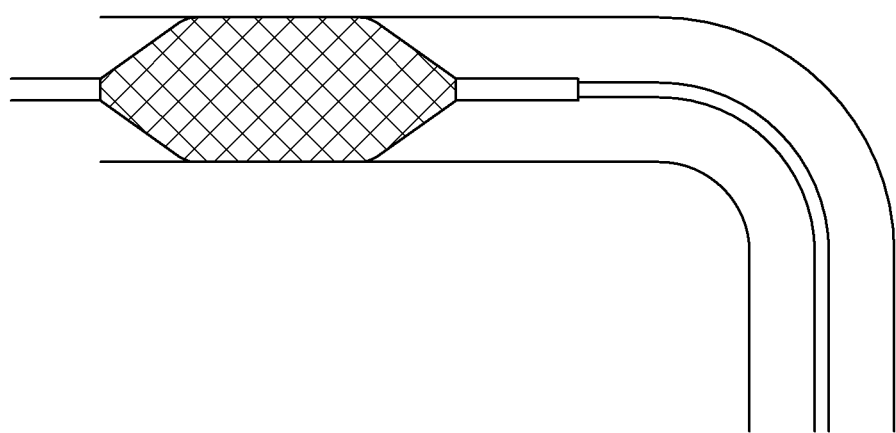
FIG. 24A is a side view of an embodiment of a rapid reperfusion device comprising an infusable temporary stent.
Figure 24B:
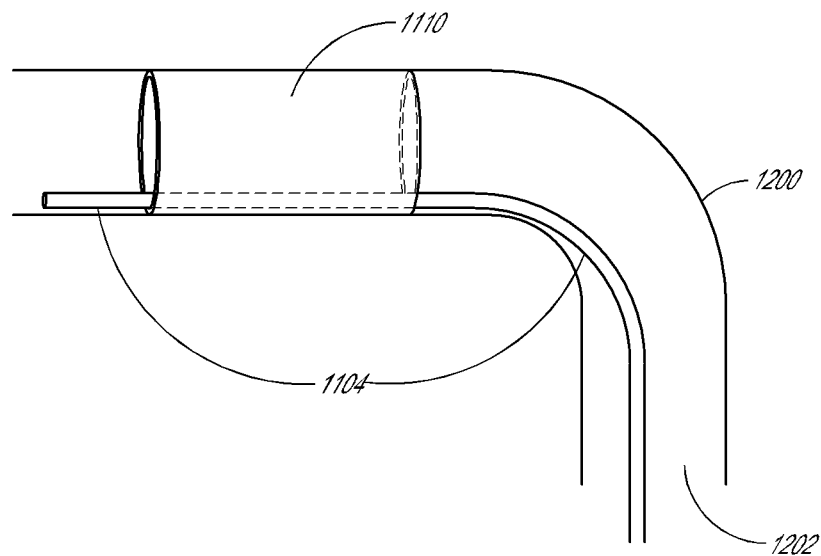
FIG. 24B is a side view of an embodiment of a rapid reperfusion device comprising an inflatable balloon.

In some embodiments, the rapid reperfusion device comprises an infusable temporary stent as illustrated in FIG. 24A. According to embodiments illustrated by FIG. 24B, an infusable balloon is connected to microcatheter 1100 and comprises active segment 1110. Inflation of the infusable balloon opens a channel through the embolus and begins the lytic process.

Figure 25A:
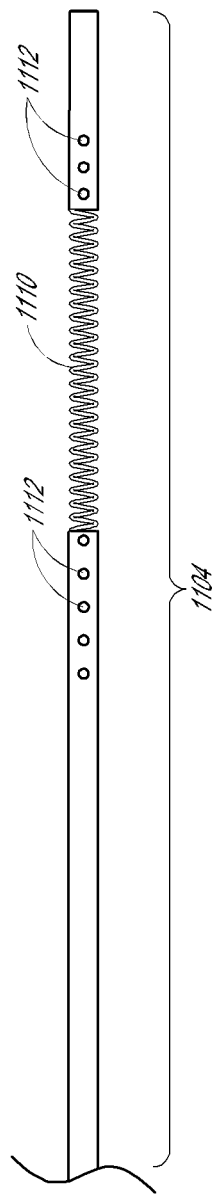
FIGS. 25A and 25B are perspective views of an embodiment of a rapid perfusion device wherein the active segment comprises a radially expandable wire.
Figure 25B:
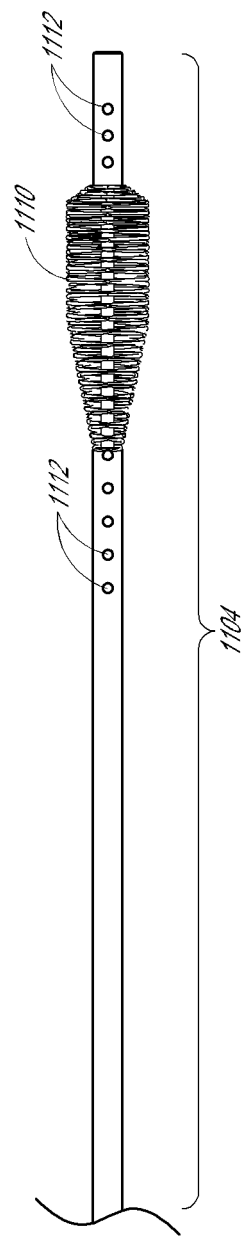

FIGS. 25A-27D illustrate exemplary embodiments wherein active segment 1110 comprises different configurations designed to reperfuse an occluded blood vessel. According to embodiments illustrated in FIGS. 25A and 25B, active segment 1110 comprises an expandable coiled wire. The coiled wire may be made from stainless steel wire or braid, composite metal polymers, memory shape alloys such as nitinol, etc., wherein the coil is able to stably expand and return to its original state. As illustrated in FIG. 25A, the diameter of coil is substantially the same as that of microcatheter 1100 when in a nonexpanded state. However, when expanded (as illustrated in FIG. 25B) coil expands radially according to the reperfusion principles disclosed herein. According to embodiments, revascularization ports 1112 provide for increased blood flow through the lumen of microcatheter 1100. Activation of the coil may occur as previously disclosed, for example mechanically using activation member 1120, or by electrical or heat methods, as well known and understood by artisans.

FIGS. 26A-26D illustrate an embodiment of the present disclosure wherein active segment 1110 comprises a tethered mesh. According to this embodiment, active segment 1110 comprises mesh 1110A and tethers 1110B. Mesh is the same as previously described. According to embodiments, mesh comprises an open braid or a covered braid. The covering comprises, according to embodiments, a distal protection mechanism and may be a polymer, such as polyurethane, or other biocompatible cover materials such as ePTFE or related thin film. Tethers 1110B serve to provide structure for mesh 1110A, while providing large openings whereby blood may freely flow from the proximal to distal end of active segment 1110. Those skilled in the art will readily understand that materials for tethers and mesh may be the same, different, or interchangeable, as needed. FIG. 26E illustrates an embodiment of an active segment comprising an open braid or covered braid configured to be connected to the microcatheter via tethers or an open braid at both the proximal and distal end, thereby forming an open proximal end and an open distal end.

Figure 26B:
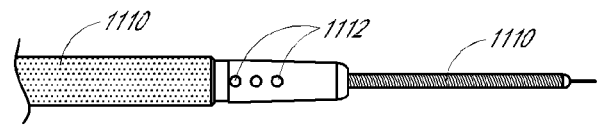
FIGS. 26A-26D are perspective views of an embodiment of a rapid perfusion device wherein the active segment comprises a covered or uncovered mesh connected to the microcatheter via tethers.
Figure 26A:
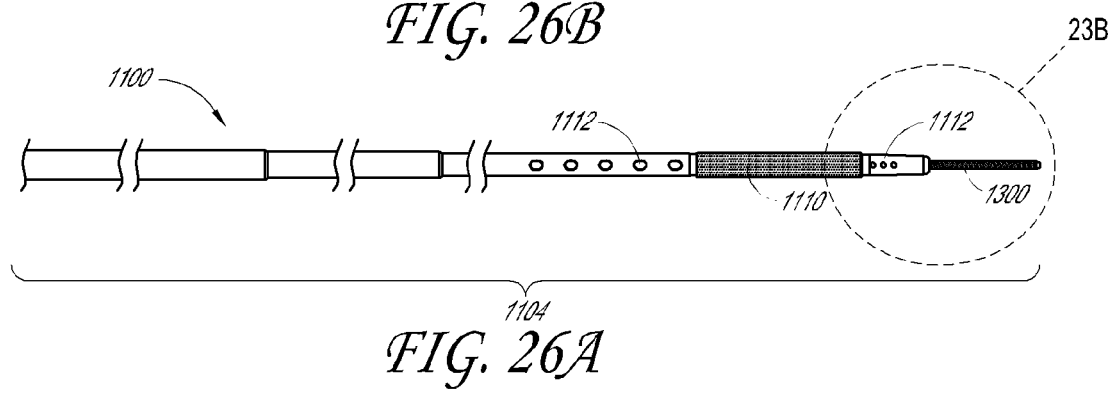
Figure 26D:
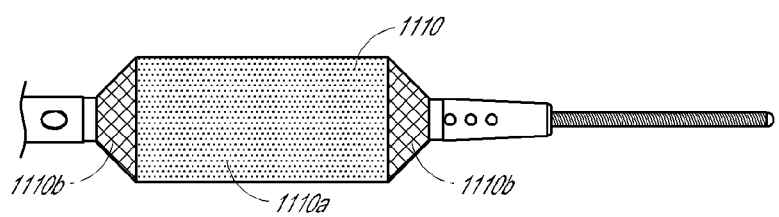
Figure 26C:
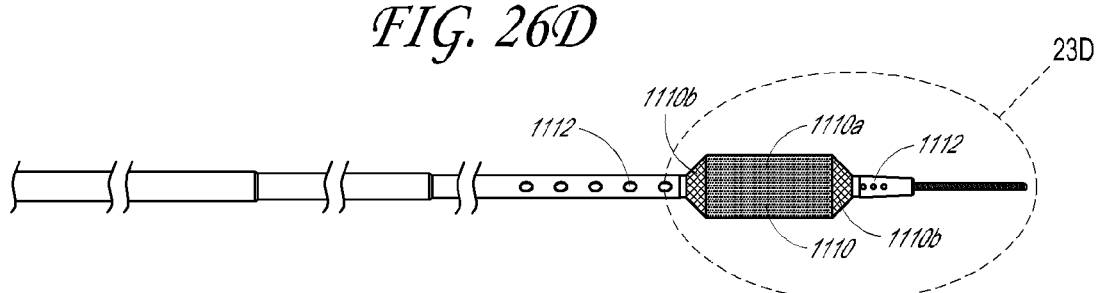
Figure 26E:
FIG. 26E is a side view of an embodiment of an active segment comprising an open braid or covered braid configured to be connected to the microcatheter via tethers or an open braid on both the proximal and distal ends.

As shown in FIGS. 26A and 26B, microcatheter 1100 is inserted along guidewire 1300. In some embodiments, guidewire 1300 is compatible with 0.010" and 0.014". Active segment is initially in a non-expanded configuration. FIGS. 26C and 26D illustrate embodiments of active segment 1110 when extended. In some embodiments, active segment 1110 has an expanded diameter from 1.5 mm to 3.5 mm and therapeutic lengths of 8 mm, 12 mm, or 16 mm. In one embodiment, microcatheter 1100 has a useable length of 150 cm.

Figure 27B:
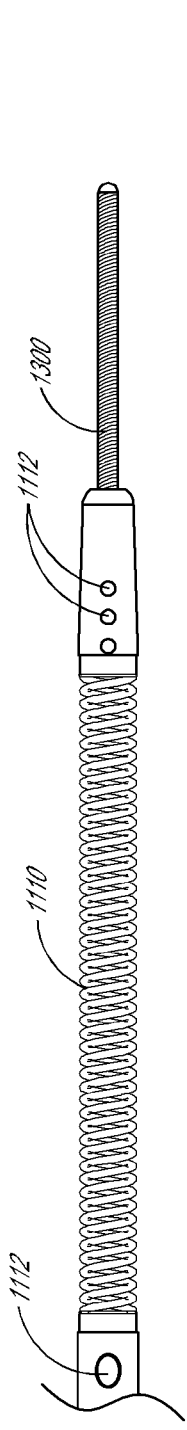
FIGS. 27A-27D are perspective views of an embodiment of a rapid perfusion device wherein the active segment comprises a radially expanding wire mesh.
Figure 27A:
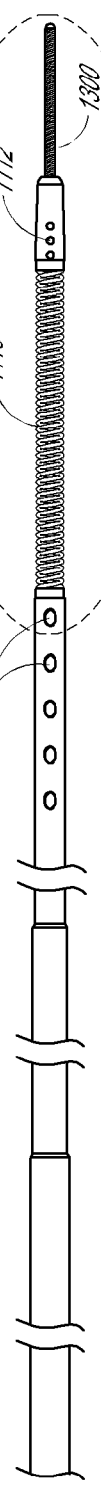
Figure 27C:
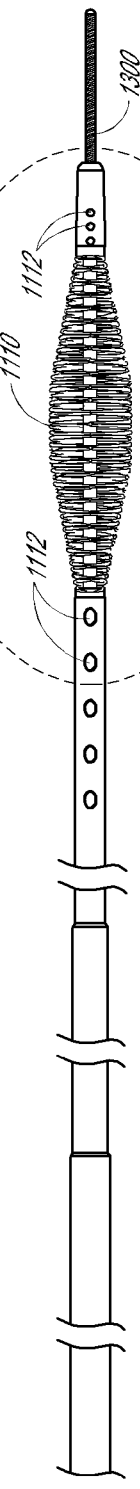
Figure 27D:
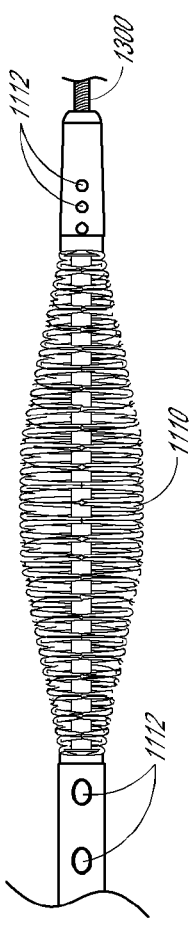

According to embodiments illustrated in FIGS. 27A-27D, active segment 1110 comprises a wire mesh having variable spacing between the wires. FIGS. 27A and 27B illustrate active segment 1110 in a non-expanded configuration. FIGS. 27C and 27D illustrate active segment 1110 in an expanded position, as disclosed herein. In some embodiments, guidewire 1300 is compatible with 0.010" and 0.014". In some embodiments, active segment 1110 has an expanded diameter from 1.5 mm to 3.5 mm and therapeutic lengths of 8 mm, 12 mm, or 16 mm. In one embodiment, microcatheter 1100 has a useable length of 150 cm.

While the apparatus and method have been described in terms of what are presently considered to be the most practical and preferred embodiments, it is to be understood that the invention need not be limited to the disclosed embodiments. It is intended to cover various modifications and similar arrangements included within the spirit and scope of the claims, the scope of which should be accorded the broadest interpretation so as to encompass all such modifications and similar structures. The present invention includes any and all embodiments of the following claims.

It should also be understood that a variety of changes may be made without departing from the essence of the invention. Such changes are also implicitly included in the description. They still fall within the scope of this invention. It should be understood that this invention is intended to yield a patent covering numerous aspects of the invention both independently and as an overall system and in both method and apparatus modes.

Further, each of the various elements of the invention and claims may also be achieved in a variety of manners. This invention should be understood to encompass each such variation, be it a variation of an embodiment of any apparatus embodiment, a method or process embodiment, or even merely a variation of any element of these.

Particularly, it should be understood that as the invention relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a invention of the action which that physical element facilitates.

Any patents, publications, or other references mentioned in this application for patent are hereby incorporated by reference. In addition, as to each term used it should be understood that unless its utilization in this application is inconsistent with such interpretation common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Invention Statement or other information statement filed with the application are hereby appended and hereby incorporated by reference; however, as to each of the above, to the extent that such information or statements incorporated by reference might be considered inconsistent with the patenting of this/ these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term comprise or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A system for the removal of emboli within neurovasculature comprising:
    a temporary reperfusion device;
        wherein said reperfusion device comprises a pusher and a self-expanding distal nitinol device eccentrically tethered to the pusher with a plurality of tethers to facilitate withdrawal of said reperfusion device;
        wherein said self-expanding distal nitinol device is configured for placement and expansion within an embolus to facilitate blood flow by compressing the embolus, said blood flow causing lysis of at least a portion of the embolus;
    wherein said self-expanding distal nitinol device comprises a generally cylindrical body having an open proximal end and an open distal end;
    wherein, when said generally cylindrical body is in an expanded state, the generally cylindrical body further facilitates blood flow by providing continuous radial pressure at the location of the embolus to enhance natural lysis of the embolus;
    a mesh basket tethered to the pusher and having at least an undeployed state and a deployed state, the mesh basket being configured to be inserted into neurovasculature in the undeployed state and removed from the neurovasculature in its deployed state;
    wherein the mesh basket is configured for retrieving all or part of any remaining portion of the embolus post reperfusion;
    wherein the mesh basket has a closed distal end;
    wherein the mesh basket is configured to be deployed into its deployed state distal to at least a section of any remaining embolus portion and expanded to capture the remaining embolus portion;
    wherein the mesh basket is suitable for deployment above the subclavian artery and common carotid artery; and
    wherein the mesh basket has radiopacity at a distal end of the mesh basket.

2. The system of claim 1, said radiopacity further comprised of at least a peg, selected from the group consisting of platinum and gold, the peg being pressed into pre-laser cut apertures at a distal end of the mesh basket.

3. The system of claim 1, wherein a polymeric liner is incorporated within the pusher to improve guidewire trackability.

4. The system of claim 3, wherein the polymeric liner is extended beyond the distal tip of the pusher.

5. The system of claim 4 whereby guidewire entanglement in the nitinol device is prevented, by the extended polymeric liner.

6. The system of claim 5, wherein the mesh basket further comprises uniform cells.

7. The system of claim 1, wherein the mesh basket is eccentrically tethered to the pusher.

8. A system for removing an embolus within neurovasculature, comprising:
    a microcatheter configured to be inserted to a position such that a distal end of the microcatheter is distal to the embolus;
    a temporary capture device configured to be inserted through the microcatheter to a location distal to a portion of the embolus, said capture device comprising an elongate member and a self-expanding distal device eccentrically tethered to the elongate member with a plurality of tethers to facilitate withdrawal of said capture device; and
    a mesh basket having an open proximal end and a closed distal end and being tethered to the elongate member for deployment distal to said capture device;
    wherein said self-expanding distal device is configured for placement and expansion within the embolus to facilitate increased blood flow by compressing the embolus, thereby enhancing natural lysis of the embolus due to the increased blood flow;
    wherein said self-expanding distal device comprises a generally cylindrical body having an open distal end;
    wherein the capture device is configured to be deployed and removed;
    wherein the self-expanding device is configured to capture at least a portion of the embolus on an external surface of the generally cylindrical body.

9. The system of claim 8, wherein said generally cylindrical body comprises an open-cell structure configured to grab at least a portion of the embolus.

10. The system of claim 8, wherein said generally cylindrical body comprises a woven pattern.

11. The system of claim 8, wherein the mesh basket is configured for offset deployment.

12. A system for removing an embolus within neurovasculature, comprising:
    a microcatheter configured to be inserted to a location such that a distal end of the microcatheter is distal to the embolus;
    a temporary reperfusion device configured to be delivered through the microcatheter, said reperfusion device comprising an elongate member and a self-expanding distal device eccentrically tethered to the elongate member with a plurality of tethers to facilitate withdrawal of said reperfusion device; and
    an embolus capture basket having an open proximal end and a closed distal end, the embolus capture basket being tethered to the elongate member for deployment distal to said reperfusion device;
    wherein said reperfusion device is configured for placement and expansion within an embolus to facilitate blood flow by compressing the embolus;
    wherein said self-expanding distal device comprises a generally cylindrical body having an open proximal end and an open distal end;

wherein, in use, the microcatheter is advanced to a location such that a distal end of the microcatheter is distal to the embolus and then the self-expanding distal device is deployed within the embolus to create a channel for blood flow, thereby providing vessel reperfusion due to natural lytic action; and wherein said reperfusion device is configured to capture at least a portion of the embolus post reperfusion on an external surface of the generally cylindrical body.

13. The system of claim 12, wherein said generally cylindrical body comprises an open-cell structure configured to grab at least a portion of the embolus.

14. The system of claim 12, wherein said generally cylindrical body comprises a woven pattern.

15. The system of claim 12, wherein the embolus capture basket is configured for offset deployment such that the embolus capture basket occupies about the center of vessel when deployed along an offset guidewire.

* * * * *